(12) United States Patent
Roeber et al.

(10) Patent No.: US 11,406,533 B2
(45) Date of Patent: Aug. 9, 2022

(54) INTEGRATED AQUEOUS SHUNT FOR GLAUCOMA TREATMENT

(71) Applicant: W. L. Gore & Associates, Inc., Newark, DE (US)

(72) Inventors: Peter J. Roeber, Oxford, PA (US); Jeffrey C. Towler, Wilmington, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 745 days.

(21) Appl. No.: 15/922,692

(22) Filed: Mar. 15, 2018

(65) Prior Publication Data

US 2018/0263817 A1   Sep. 20, 2018

Related U.S. Application Data

(60) Provisional application No. 62/473,090, filed on Mar. 17, 2017.

(51) Int. Cl.
*A61F 9/007* (2006.01)
*A61L 31/04* (2006.01)
(Continued)

(52) U.S. Cl.
CPC ........ *A61F 9/00781* (2013.01); *A61L 31/048* (2013.01); *A61L 31/146* (2013.01); *A61M 27/00* (2013.01); *A61F 9/0017* (2013.01); *A61F 2210/0076* (2013.01); *A61F 2230/0091* (2013.01); *A61F 2240/001* (2013.01);
(Continued)

(58) Field of Classification Search
CPC ................ A61F 9/00781; A61F 9/0017; A61F 2240/001; A61L 31/048; A61L 31/146; A61M 27/00
See application file for complete search history.

(56) References Cited

U.S. PATENT DOCUMENTS 3,618,604 A   11/1971 Ness
3,683,928 A   8/1972 Kuntz
(Continued)

FOREIGN PATENT DOCUMENTS

AU   06600/12 B2   6/1995
CA   2502761 A1   4/1997
(Continued)

OTHER PUBLICATIONS

International Preliminary Report on Patentability received for PCT Patent Application No. PCT/US2018/022922, dated Sep. 26, 2019, 9 pages.

(Continued)

*Primary Examiner* — Ariana Zimbouski

(57) ABSTRACT

Glaucoma treatment devices are disclosed. In various example, the glaucoma treatment devices include multiple microporous layers arranged together to form a microporous body configured to help facilitate evacuation of fluid from a fluid-filled body cavity, and reabsorption of the evacuated aqueous humor by the body through tissue surrounding the glaucoma treatment device. In some examples, the glaucoma treatment device includes one or more portions configured to resist cellular ingrowth, and one or more portions configured to permit cellular ingrowth.

22 Claims, 11 Drawing Sheets

(51) Int. Cl.
A61L 31/14 (2006.01)
A61M 27/00 (2006.01)
A61F 9/00 (2006.01)

(52) U.S. Cl.
CPC .............. A61F 2250/0003 (2013.01); A61F 2250/0023 (2013.01); A61F 2250/0051 (2013.01); A61F 2250/0059 (2013.01); A61L 2430/16 (2013.01); A61M 27/002 (2013.01); A61M 2205/04 (2013.01); A61M 2205/3334 (2013.01); A61M 2205/3341 (2013.01); A61M 2210/0612 (2013.01)

(56) References Cited

U.S. PATENT DOCUMENTS

| | | |
|---|---|---|
| 3,828,777 A | 8/1974 | Ness |
| 3,960,150 A | 6/1976 | Hussain et al. |
| 3,962,414 A | 6/1976 | Michaels |
| 4,014,335 A | 3/1977 | Arnold |
| 4,182,342 A | 1/1980 | Smith |
| 4,579,221 A | 4/1986 | Corella |
| 4,759,759 A | 7/1988 | Walker et al. |
| 5,037,434 A | 8/1991 | Lane |
| 5,147,647 A | 9/1992 | Darougar |
| 5,163,955 A | 11/1992 | Love et al. |
| 5,282,851 A | 2/1994 | Jacob-LaBarre |
| 5,378,475 A | 1/1995 | Smith et al. |
| 5,423,777 A | 6/1995 | Tajiri et al. |
| 5,681,275 A | 10/1997 | Ahmed |
| 5,702,414 A | 12/1997 | Richter et al. |
| 5,708,044 A | 1/1998 | Branca |
| 5,713,953 A | 2/1998 | Vallana et al. |
| 5,773,019 A | 6/1998 | Ashton et al. |
| 5,861,028 A | 1/1999 | Angell |
| 5,882,327 A | 3/1999 | Jacob |
| 5,928,281 A | 7/1999 | Huynh et al. |
| 5,935,163 A | 8/1999 | Gabbay |
| 6,074,419 A | 6/2000 | Healy et al. |
| 6,086,612 A | 7/2000 | Jansen |
| 6,142,969 A | 11/2000 | Nigam |
| 6,171,335 B1 | 1/2001 | Wheatley et al. |
| 6,174,331 B1 | 1/2001 | Moe et al. |
| 6,197,143 B1 | 3/2001 | Bodnar |
| 6,254,636 B1 | 7/2001 | Peredo |
| 6,283,995 B1 | 9/2001 | Moe et al. |
| 6,287,338 B1 | 9/2001 | Sarnowski et al. |
| 6,364,905 B1 | 4/2002 | Simpson et al. |
| 6,432,542 B1 | 8/2002 | Tsai |
| 6,450,984 B1 | 9/2002 | Lynch et al. |
| 6,541,589 B1 | 4/2003 | Baillie |
| 6,562,069 B2 | 5/2003 | Cai et al. |
| 6,613,086 B1 | 9/2003 | Moe et al. |
| 6,613,087 B1 | 9/2003 | Healy et al. |
| 6,696,526 B1 | 2/2004 | Kaulbach et al. |
| 6,699,210 B2 | 3/2004 | Williams et al. |
| 6,699,211 B2 | 3/2004 | Savage |
| 6,713,081 B2 | 3/2004 | Robinson et al. |
| 6,994,666 B2 | 2/2006 | Shannon et al. |
| 7,018,404 B2 | 3/2006 | Holmberg et al. |
| 7,261,732 B2 | 8/2007 | Justino |
| 7,306,729 B2 | 12/2007 | Bacino et al. |
| 7,320,705 B2 | 1/2008 | Quintessenza |
| 7,331,993 B2 | 2/2008 | White |
| 7,361,189 B2 | 4/2008 | Case et al. |
| 7,462,675 B2 | 12/2008 | Chang et al. |
| 7,531,611 B2 | 5/2009 | Sabol et al. |
| 7,604,663 B1 | 10/2009 | Reimink et al. |
| 7,833,565 B2 | 11/2010 | O'Connor et al. |
| 7,862,610 B2 | 1/2011 | Quintessenza |
| 8,216,631 B2 | 7/2012 | O'Connor et al. |
| 8,219,229 B2 | 7/2012 | Cao et al. |
| 8,246,676 B2 | 8/2012 | Acosta et al. |
| 8,267,994 B2 | 9/2012 | Jin |
| 8,273,101 B2 | 9/2012 | Garcia et al. |
| 8,303,647 B2 | 11/2012 | Case |
| 8,399,006 B2 | 3/2013 | De Juan, Jr. et al. |
| 8,545,430 B2 | 10/2013 | Silvestrini |
| 8,556,960 B2 | 10/2013 | Agnew et al. |
| 8,632,489 B1 | 1/2014 | Ahmed |
| 8,637,144 B2 | 1/2014 | Ford |
| 8,690,939 B2 | 4/2014 | Miller |
| 8,834,406 B2 | 9/2014 | Snyder et al. |
| 8,834,911 B2 | 9/2014 | Glezer et al. |
| 8,961,593 B2 | 2/2015 | Bonhoeffer et al. |
| 8,961,599 B2 | 2/2015 | Bruchman et al. |
| 8,961,600 B2 | 2/2015 | Nissan et al. |
| 9,139,669 B2 | 9/2015 | Xu et al. |
| 9,155,610 B2 | 10/2015 | Soletti et al. |
| 9,155,618 B2 | 10/2015 | Kalmann et al. |
| 9,259,313 B2 | 2/2016 | Wheatley |
| 9,301,835 B2 | 4/2016 | Campbell et al. |
| 9,301,837 B2 | 4/2016 | Beith |
| 9,326,891 B2 | 5/2016 | Horvath et al. |
| 9,364,322 B2 | 6/2016 | Conklin et al. |
| 9,370,444 B2 | 6/2016 | Cunningham, Jr. |
| 9,539,089 B2 | 1/2017 | Beith |
| 9,572,713 B2 | 2/2017 | Lind et al. |
| 9,636,219 B2 | 5/2017 | Keidar et al. |
| 9,636,254 B2 | 5/2017 | Yu et al. |
| 9,655,720 B2 | 5/2017 | Bluestein et al. |
| 9,675,453 B2 | 6/2017 | Guttenberg et al. |
| 9,833,314 B2 | 12/2017 | Corbett |
| 9,849,629 B2 | 12/2017 | Zagl et al. |
| 9,987,120 B2 | 6/2018 | Soletti et al. |
| 9,999,500 B2 | 6/2018 | Greenslet et al. |
| 10,052,200 B2 | 8/2018 | Chung et al. |
| 10,195,023 B2 | 2/2019 | Wrobel |
| 10,299,915 B2 | 5/2019 | Edelman et al. |
| 10,307,292 B2 | 6/2019 | Litvin |
| 10,413,402 B2 | 9/2019 | Squara |
| 10,413,403 B2 | 9/2019 | Boden et al. |
| 10,426,609 B2 | 10/2019 | Edelman et al. |
| 10,433,955 B2 | 10/2019 | Edelman et al. |
| 10,512,537 B2 | 12/2019 | Corbett et al. |
| 10,588,746 B2 | 3/2020 | Bernstein et al. |
| 10,603,164 B2 | 3/2020 | Girard et al. |
| 2002/0106395 A1 | 8/2002 | Brubaker |
| 2002/0110635 A1 | 8/2002 | Brubaker et al. |
| 2002/0156413 A1 | 10/2002 | Williams et al. |
| 2002/0198594 A1 | 12/2002 | Schreck |
| 2003/0027332 A1 | 2/2003 | Lafrance et al. |
| 2003/0088260 A1 | 5/2003 | Smedley et al. |
| 2003/0094731 A1 | 5/2003 | Simpson |
| 2003/0109923 A1 | 6/2003 | Chinn et al. |
| 2004/0024345 A1 | 2/2004 | Gharib et al. |
| 2004/0215333 A1 | 10/2004 | Duran et al. |
| 2005/0085892 A1 | 4/2005 | Goto et al. |
| 2005/0137538 A1 | 6/2005 | Kunzler et al. |
| 2005/0171507 A1 | 8/2005 | Christian et al. |
| 2005/0182350 A1 | 8/2005 | Nigam |
| 2005/0228487 A1 | 10/2005 | Kujawski |
| 2005/0234546 A1 | 10/2005 | Nugent et al. |
| 2005/0261759 A1 | 11/2005 | Lambrecht et al. |
| 2005/0266047 A1 | 12/2005 | Tu et al. |
| 2005/0273033 A1 | 12/2005 | Grahn et al. |
| 2006/0109923 A1 | 5/2006 | Cai et al. |
| 2006/0189917 A1 | 8/2006 | Mayr et al. |
| 2006/0195187 A1 | 8/2006 | Stegmann et al. |
| 2006/0258994 A1 | 11/2006 | Avery |
| 2007/0078371 A1 | 4/2007 | Brown et al. |
| 2007/0083184 A1 | 4/2007 | Simpson |
| 2007/0088432 A1 | 4/2007 | Solovay et al. |
| 2007/0118147 A1 | 5/2007 | Smedley et al. |
| 2007/0293872 A1 | 12/2007 | Peyman |
| 2008/0071361 A1 | 3/2008 | Tuval et al. |
| 2008/0082161 A1 | 4/2008 | Woo |
| 2008/0091261 A1 | 4/2008 | Long et al. |
| 2008/0133005 A1 | 6/2008 | Andrieu et al. |
| 2008/0200977 A1 | 8/2008 | Paul et al. |
| 2008/0264993 A1 | 10/2008 | Schulte et al. |
| 2008/0312737 A1 | 12/2008 | Jin |
| 2009/0157175 A1 | 6/2009 | Benichou |
| 2009/0240320 A1 | 9/2009 | Tuval et al. |

(56) References Cited

U.S. PATENT DOCUMENTS

| | | |
|---|---|---|
| 2009/0299469 A1 | 12/2009 | Kollar |
| 2010/0015200 A1* | 1/2010 | McClain ............ A61L 17/005 424/423 |
| 2010/0082094 A1 | 4/2010 | Quadri et al. |
| 2010/0114307 A1 | 5/2010 | Agnew et al. |
| 2010/0114309 A1 | 5/2010 | De et al. |
| 2010/0119580 A1 | 5/2010 | Guo et al. |
| 2010/0137981 A1 | 6/2010 | Silvestrini et al. |
| 2010/0161040 A1 | 6/2010 | Braido et al. |
| 2010/0168644 A1 | 7/2010 | Brown |
| 2010/0168839 A1 | 7/2010 | Braido et al. |
| 2010/0185277 A1 | 7/2010 | Braido et al. |
| 2010/0241046 A1 | 9/2010 | Pinchuk et al. |
| 2011/0112620 A1 | 5/2011 | Du |
| 2011/0196487 A1 | 8/2011 | Badawi et al. |
| 2011/0244014 A1 | 10/2011 | Williams et al. |
| 2011/0257738 A1 | 10/2011 | Corbett et al. |
| 2011/0270388 A9 | 11/2011 | Stevens |
| 2011/0276128 A1 | 11/2011 | Cao et al. |
| 2011/0282440 A1 | 11/2011 | Cao et al. |
| 2012/0035525 A1 | 2/2012 | Silvestrini |
| 2012/0123315 A1 | 5/2012 | Horvath et al. |
| 2012/0123317 A1 | 5/2012 | Horvath et al. |
| 2012/0165720 A1 | 6/2012 | Horvath et al. |
| 2012/0197175 A1 | 8/2012 | Horvath et al. |
| 2012/0253453 A1 | 10/2012 | Bruchman et al. |
| 2012/0310137 A1 | 12/2012 | Silvestrini |
| 2012/0323315 A1 | 12/2012 | Bruchman et al. |
| 2013/0046379 A1 | 2/2013 | Paolitto et al. |
| 2013/0211314 A1 | 8/2013 | Venkatraman et al. |
| 2013/0218081 A1 | 8/2013 | Roth |
| 2013/0274691 A1 | 10/2013 | De Juan, Jr. et al. |
| 2013/0325024 A1 | 12/2013 | Nissan et al. |
| 2013/0325111 A1 | 12/2013 | Campbell et al. |
| 2014/0012371 A1 | 1/2014 | Li |
| 2014/0031927 A1 | 1/2014 | Bruchman et al. |
| 2014/0128960 A1 | 5/2014 | Greenslet et al. |
| 2014/0154321 A1 | 6/2014 | Ashton |
| 2014/0170204 A1 | 6/2014 | Desai et al. |
| 2014/0186420 A1 | 7/2014 | Utkhede et al. |
| 2014/0214158 A1 | 7/2014 | Board et al. |
| 2014/0236067 A1 | 8/2014 | Horvath et al. |
| 2014/0236068 A1 | 8/2014 | Van et al. |
| 2014/0358224 A1 | 12/2014 | Tegels et al. |
| 2015/0005689 A1 | 1/2015 | Horvath et al. |
| 2015/0119980 A1 | 4/2015 | Beith et al. |
| 2015/0224200 A1 | 8/2015 | De Juan, Jr. et al. |
| 2015/0224231 A1 | 8/2015 | Bruchman et al. |
| 2015/0320975 A1 | 11/2015 | Simpson et al. |
| 2015/0374545 A1 | 12/2015 | Horvath et al. |
| 2016/0015516 A1 | 1/2016 | Bernstein et al. |
| 2016/0038412 A1 | 2/2016 | Guo et al. |
| 2016/0058616 A1 | 3/2016 | Camras et al. |
| 2016/0067032 A1 | 3/2016 | Soletti et al. |
| 2016/0100939 A1 | 4/2016 | Armstrong et al. |
| 2016/0153591 A1 | 6/2016 | Fonfara et al. |
| 2016/0245432 A1 | 8/2016 | Fonfara et al. |
| 2016/0256321 A1 | 9/2016 | Horvath et al. |
| 2016/0256382 A1 | 9/2016 | Shi et al. |
| 2016/0287513 A1 | 10/2016 | Rakic et al. |
| 2016/0296322 A1 | 10/2016 | Edelman et al. |
| 2016/0302965 A1 | 10/2016 | Erickson et al. |
| 2016/0302967 A1 | 10/2016 | Ahn |
| 2016/0331528 A1 | 11/2016 | Parker et al. |
| 2016/0374856 A1 | 12/2016 | Pinchuk et al. |
| 2017/0000610 A1 | 1/2017 | Eppihimer et al. |
| 2017/0014227 A1 | 1/2017 | Boden et al. |
| 2017/0071729 A1 | 3/2017 | Wrobel |
| 2017/0079779 A1 | 3/2017 | Tabor |
| 2017/0079782 A1 | 3/2017 | Beith |
| 2017/0156854 A1 | 6/2017 | Hammer |
| 2017/0172794 A1 | 6/2017 | Varner et al. |
| 2017/0189175 A1 | 7/2017 | Justino et al. |
| 2017/0245989 A1 | 8/2017 | Bluestein et al. |
| 2017/0252156 A1 | 9/2017 | Bernstein et al. |
| 2017/0296783 A1 | 10/2017 | Connolly et al. |
| 2017/0367888 A1 | 12/2017 | Brown |
| 2018/0049872 A1 | 2/2018 | Bennett |
| 2018/0125632 A1 | 5/2018 | Cully et al. |
| 2018/0133002 A1 | 5/2018 | Yi et al. |
| 2018/0177592 A1 | 6/2018 | Benichou et al. |
| 2018/0185151 A1 | 7/2018 | Bishop |
| 2018/0263775 A1 | 9/2018 | Shah |
| 2018/0263818 A1 | 9/2018 | Roeber et al. |
| 2018/0263819 A1 | 9/2018 | Roeber et al. |
| 2018/0344457 A1 | 12/2018 | Gross et al. |
| 2019/0015191 A1 | 1/2019 | Berdajs |
| 2019/0091014 A1 | 3/2019 | Arcaro et al. |
| 2019/0091015 A1 | 3/2019 | Dienno et al. |
| 2019/0125529 A1 | 5/2019 | Colavito et al. |
| 2019/0125530 A1 | 5/2019 | Arcaro et al. |
| 2019/0125531 A1 | 5/2019 | Bennett et al. |
| 2019/0282360 A1 | 9/2019 | Colavito et al. |
| 2019/0343617 A1 | 11/2019 | Sobrino-Serrano et al. |
| 2019/0365531 A1 | 12/2019 | Beith |
| 2020/0113681 A1 | 4/2020 | Armstrong et al. |
| 2020/0121454 A1 | 4/2020 | Spence |
| 2020/0188114 A1 | 6/2020 | Radspinner et al. |
| 2021/0322217 A1 | 10/2021 | Roeber et al. |

FOREIGN PATENT DOCUMENTS

| | | |
|---|---|---|
| CN | 1208602 A | 2/1999 |
| CN | 2414757 Y | 1/2001 |
| CN | 1285724 A | 2/2001 |
| CN | 101965211 A | 2/2011 |
| CN | 202619978 U | 12/2012 |
| CN | 103179927 A | 6/2013 |
| CN | 105579001 A | 5/2016 |
| CN | 205198254 U | 5/2016 |
| EP | 2349147 B1 | 3/2015 |
| EP | 2958530 A1 | 12/2015 |
| GB | 2513194 A | 10/2014 |
| JP | 11-505159 A | 5/1999 |
| JP | 2000-513248 A | 10/2000 |
| JP | 2002-521145 A | 7/2002 |
| JP | 2005-500101 A | 1/2005 |
| JP | 2007-521125 | 8/2007 |
| JP | 2010-540079 A | 12/2010 |
| JP | 2012-504031 A | 2/2012 |
| JP | 2014-517720 A | 7/2014 |
| JP | 2015-039515 A | 3/2015 |
| JP | 2016-137278 A | 8/2016 |
| WO | 2001/066037 A2 | 9/2001 |
| WO | 2003/007795 A2 | 1/2003 |
| WO | 2005/076973 A2 | 8/2005 |
| WO | 2007/100408 A2 | 9/2007 |
| WO | 2008/030951 A2 | 3/2008 |
| WO | 2008/133852 A1 | 11/2008 |
| WO | 2009/042196 A2 | 4/2009 |
| WO | 2009/137785 A2 | 11/2009 |
| WO | 2010/037141 A1 | 4/2010 |
| WO | 2011/147849 A1 | 12/2011 |
| WO | 2012/018779 A2 | 2/2012 |
| WO | 2012/135603 A2 | 10/2012 |
| WO | 2013/090006 A1 | 6/2013 |
| WO | 2013/096854 A3 | 8/2013 |
| WO | 2014/028725 A1 | 2/2014 |
| WO | 2014/130574 A1 | 8/2014 |
| WO | 2014/145811 A1 | 9/2014 |
| WO | 2015/065646 A1 | 5/2015 |
| WO | 2016/033270 A1 | 3/2016 |
| WO | WO2016168686 | 10/2016 |
| WO | 2016/196841 A1 | 12/2016 |
| WO | 2018/150392 A1 | 8/2018 |
| WO | 2018/170429 A1 | 9/2018 |
| WO | 2018/170433 A1 | 9/2018 |

(56) References Cited

FOREIGN PATENT DOCUMENTS

| WO | 2018/187714 A1 | 10/2018 |
|---|---|---|
| WO | 2019/154927 A1 | 8/2019 |

OTHER PUBLICATIONS

International Preliminary Report on Patentability received for PCT Patent Application No. PCT/US2018/022929, dated Sep. 26, 2019, 9 pages.
International Preliminary Report on Patentability received for PCT Patent Application No. PCT/US2018/022933, dated Sep. 26, 2019, 9 pages.
International Search Report of PCT/2018/022933 dated Jul. 3, 2018.
International Search Report of PCT/US2018/022929 dated Jun. 28, 2018.
International Search Report dated Jul. 23, 2018 for PCT/US2018/022922.
Han, et al. "Membrane-tube-type glaucoma shunt device for refractory glaucoma surgery", Glaucoma, Graefes Arch Clin Exp Ophthalmol, DOI 10.1007/s00417-016-3510-z. Springer-Verlag Berlin Heidelberg 2016.
Ando et al., Ten-year experience with handmade trileaflet polytetrafluoroethylene valved conduit used for pulmonary reconstruction. The Journal of Thoracic and Cardiovascular Surgery, Jan. 2009, vol. 137, No. 1, pp. 124-131.
Gedde et al., "Treatment Outcomes in the Tube Versus Trabeculectomy (TVT) Study After Five Years of Follow-up", Am J Ophthalmol., vol. 153, No. 5, 2012, pp. 789-803.
International Preliminary Report on Patentability received for PCT Patent Application No. PCT/US2015/055348, dated Apr. 27, 2017, 18 pages.
International Preliminary Report on Patentability received for PCT Patent Application No. PCT/US2019/048759, dated Mar. 11, 2021, 12 pages.
International Preliminary Report on Patentability received for PCT Patent Application No. PCT/US2019/048760, dated Mar. 11, 2021, 9 pages.
International Search Report and Written Opinion received for PCT Patent Application No. PCT/US2015/055348, dated Apr. 11, 2016, 23 pages.
International Search Report and Written Opinion received for PCT Patent Application No. PCT/US2018/050771, dated Feb. 25, 2019, 16 pages.
International Search Report and Written Opinion received for PCT Patent Application No. PCT/US2019/048759, dated Feb. 12, 2020, 16 pages.
International Search Report and Written Opinion received for PCT Patent Application No. PCT/US2019/048760, dated Dec. 3, 2019, 15 pages.
International Search Report and Written Opinion received for PCT Patent Application No. PCT/US2019/065890, dated Mar. 18, 2020, 9 pages.
International Search Report and Written Opinion for PCT/US2015/055348 dated Apr. 11, 2016, corresponding to U.S. Appl. No. 14/881,124, 6 pages.
Invitation to Pay Additional Fees received for PCT Patent Application No. PCT/US2019/048759, dated Dec. 11, 2019, 10 pages.
Karthikeyan et al., "The concept of ocular inserts as drug delivery systems: An overview", Asian Journal of Pharmaceutics, vol. 2, No. 4, 2008, pp. 192-200.
Lee et al., "Aqueous-Venous Shunt for Glaucoma A Further Report", Arch Opthalmol, vol. 99, 1981, pp. 2007-2012.
Lee et al., "Aqueous-Venous Shunt in The Rabbit Eye: A Long-Term Follow-Up", Trans. Soc. Ophthal. Sin., vol. 8, 1969, pp. 7-24.
Lee et al., "Aqueous-Venus Shunt for Glaucoma: Report on 15 cases", AnnalOphthal, Oct. 1974, pp. 1083-1088.
Lee et al., "Effect of an Aqueous-Venous Shunt In The Monkey Eye", Canad. J. Ophthal., 3:22, 1968, pp. 22-27.
Lee et al., "Effect of aqueous-venous shunt on rabbit eyes", Inivestigative Ophthalmology, vol. 5, No. 3, 1996, pp. 304-311.
Lee et al., "Glaucoma Microsurgery Aqueous-Venous Shunt Procedure", International Surgery, vol. 57, No. 1, Jan. 1972, pp. 37-41.
Miyazaki, et al., Expanded polytetrafluoroethylene conduits and patches with bulging sinuses and fan-shaped valves in right ventricular outflow tract reconstruction: Multicneter study in Japan. The Journal of Thoracic and Cardiovascular Surgery, Nov. 2011, vol. 142, No. 5, pp. 1122-1129.
Miyazaki, et al., Expanded polytetrafluoroethylene valved conduit and patch with bulging sinuses in right ventricular outflow tract reconstruction. The Journal of Thoracic and Cardiovascular Surgery, Aug. 2007, vol. 134, No. 2, pp. 327-332.
Ootaki et al., Medium-term outcomes after implantation of expanded polytetrafluoroethylene valved conduit. The Annals of Thoracic Surgery, 2018; 105 (3), pp. 843-850.
Rese et al., "Sustained drug delivery in glaucoma", Current Opinion in Ophthalmology, vol. 25, No. 2, 2014, pp. 112-117.
Shinkawa et al., Valved polytetrafluoroethylene conduits for right ventricular outflow tract reconstruction. The Annals of Thoracic Surgery. Jul. 2015; 100(1), pp. 129-137.
Stevenson et al., "Reservoir-Based Drug Delivery Systems Utilizing Microtechnology", Advanced Drug Delivery Reviews, vol. 64, No. 14, 2012, pp. 1590-1602.
Understanding Your Heart Valve. Medtronic USA, Inc., 2006. Pamphlet.
Yamagishi et al. Outflow reconstruction of tetralogy of fallot using a Gore-Tex valve. The Anals of Thoracic Surgery, Dec. 1993; 56(6), pp. 1414-1417.

\* cited by examiner

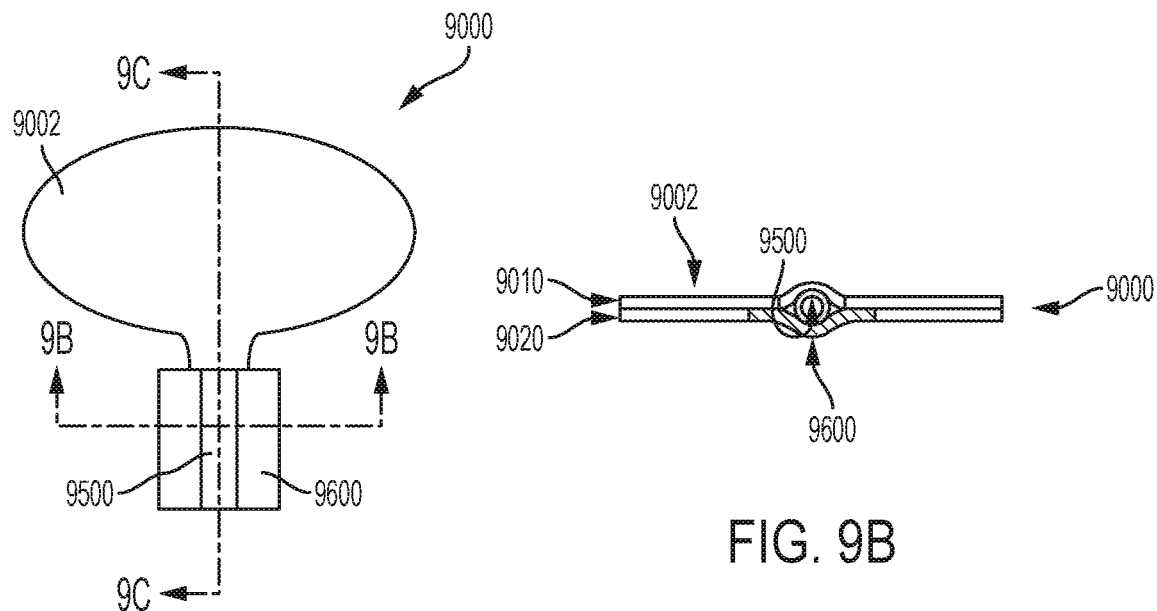
FIG. 9A
FIG. 9B
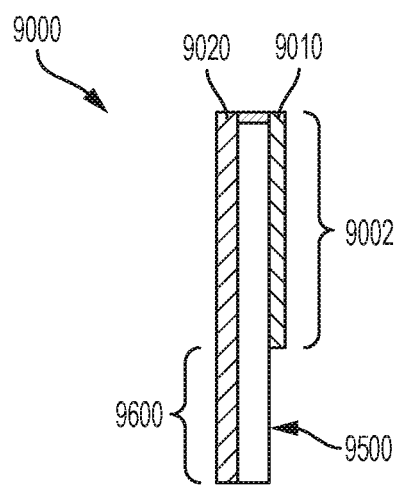
FIG. 9C

INTEGRATED AQUEOUS SHUNT FOR GLAUCOMA TREATMENT

CROSS-REFERENCE TO RELATED APPLICATION

This application claims the benefit of Provisional Application No. 62/473,090, filed Mar. 17, 2017, which is incorporated herein by reference in its entirety. This application is also relative to an application titled "DELIVERY AIDS FOR GLAUCOMA SHUNTS,", filed on the same day as this application, Mar. 15, 2018, which is incorporated herein by reference in its entirety. This application is also relative to an application titled "GLAUCOMA TREATMENT SYSTEMS AND METHODS," filed on the same day as this application, Mar. 15, 2018, which is incorporated herein by reference in its entirety.

BACKGROUND

Aqueous humor is a fluid that fills the anterior chambers of the eye and contributes to the intraocular pressure or fluid pressure inside the eye. Glaucoma is a progressive disease of the eye characterized by an increase of the eye's intraocular pressure. This increase in intraocular pressure is commonly caused by an insufficient amount of aqueous humor being reabsorbed by the body. In some cases, the aqueous humor is not absorbed fast enough or even at all, while in other cases, the aqueous humor is additionally or alternatively being produced too quickly. An increase in intraocular pressure is associated with a gradual and sometimes permanent loss of vision in the afflicted eye.

A number of attempts have been made to treat glaucoma. However, some of the conventional devices lack the flexibility, conformity, and device/tissue attachment that is required to avoid relative movement between the device and the surrounding tissue. Such movement can lead to persistent irritation of the surrounding tissue. Irritation, in turn, can lead to an augmented chronic inflammatory tissue response, excessive scar formation at the device site, and a heightened risk of device erosion through the conjunctiva and endophthalmitis. In instances where erosion does not occur, the scar tissue effectively prevents reabsorption of the aqueous humor. These complications can serve to prevent proper functioning of the device. The resulting effect is a gradual increase in intraocular pressure and progression of glaucoma.

SUMMARY

According to one example, ("Example 1"), a biological fluid drainage device includes a body including a first microporous membrane, a second microporous membrane, a third microporous membrane, and a fourth microporous membrane in a stacked configuration, the second and third microporous membranes being situated between the first and fourth microporous membranes, and an inflatable reservoir being defined between the second and third microporous membranes, wherein the second and third microporous membranes are configured to resist tissue ingrowth, and wherein the first and fourth microporous membranes are configured to permit tissue ingrowth; and a fluid conduit having a first end and a second end, the first end being fluidly coupled to the reservoir and the second end extending outside the body and being insertable into a fluid-filled body cavity such that a fluid from the fluid-filled body cavity is transferable to the reservoir.

According to another example, ("Example 2") further to Example 1, the second and third microporous membranes are partially bonded to each other such that portions of the second and third microporous membranes are free to slide relative to or separate from one another.

According to another example, ("Example 3") further to any of Examples 1 and 2, the second and third microporous membranes each have a permeability that is different from a permeability of each of the first and fourth microporous membranes.

According to another example, ("Example 4") further to any of Examples 1 to 3, at least one of the first, second, third, and fourth microporous membranes comprises expanded polytetrafluoroethylene.

According to another example, ("Example 5") further to any of the preceding Examples, the fluid is aqueous humor and the fluid filled cavity is the anterior chamber.

According to another example, ("Example 6") further to any of the preceding Examples, the device further includes a fifth microporous membrane situated adjacent the body, wherein the fifth microporous membrane extends between the body and the second end of the fluid conduit.

According to another example, ("Example 7") further to Example 6, the fifth microporous membrane is configured to permit tissue ingrowth.

According to another example, ("Example 8") further to any of Examples 6 to 7, the fifth microporous membrane is coupled to the fluid conduit.

According to another example, ("Example 9") further to any of Examples 6 to 8, the fifth microporous membrane is integral with one of the first, second, third or fourth microporous membranes.

According to another example, ("Example 10") further to Example 9, the fifth microporous membrane and the first microporous membrane are the same microporous membrane.

According to another example, ("Example 11") further to any of Examples 6 to 10, the device further includes a sixth microporous membrane situated adjacent the body, wherein the sixth microporous membrane extends between the body and the second end of the fluid conduit.

According to another example, ("Example 12") further to Example 11, the sixth microporous membrane and the fourth microporous membrane are the same microporous membrane.

According to another example, ("Example 13") further to any of Examples 11 to 12, the sixth microporous membrane includes a perforation sized to accommodate the fluid conduit such that the fluid conduit can be extended through the perforation and into the fluid-filled body cavity when implanted.

According to another example, ("Example 14") further to any of the preceding Examples, the first and fourth microporous membranes are each configured to remain permeable to the fluid after ingrowth of tissue occurs in the first and fourth microporous membranes.

According to another example, ("Example 15") further to any of the preceding Examples, the reservoir is configured to inflate when the fluid is transferred into the reservoir.

According to another example, ("Example 16") further to Example 15, the body is configured to adopt a predetermined profile as a result of inflation of the reservoir.

According to another example, ("Example 17") further to any of the preceding Examples, the first, second, third, and fourth microporous membranes each comprise a plurality of small holes, and wherein the plurality of small holes of the second and third microporous membranes are sized to resist tissue ingrowth, and wherein the plurality of small holes of the first and fourth microporous membranes are sized to permit tissue ingrowth.

According to another example, ("Example 18"), further to any of the preceding examples, one of the second and third microporous membranes is hydrophobic and one of the first fourth microporous membranes are hydrophilic. According to another example, further to any of the preceding examples, the first, second, third, and fourth microporous membranes are hydrophobic. According to another example, further to any of the preceding examples, the first, second, third, and fourth microporous membranes are hydrophilic.

According to another example, ("Example 19"), further to any of the preceding examples, one of the first, second, third, and fourth microporous membranes is formed of a plurality of microporous layers of expanded polytetrafluoroethylene.

According to another example, ("Example 20"), an aqueous humor diffusion device includes a first proliferation diffusion membrane configured to permit tissue ingrowth; a first constriction diffusion membrane configured to resist tissue ingrowth, the first constriction diffusion membrane being coupled to the first proliferation diffusion membrane; a second constriction diffusion membrane configured to resist tissue ingrowth, the second constriction diffusion membrane being coupled to the first constriction diffusion membrane such that a first region of the second constriction diffusion membrane is coupled to the first constriction diffusion membrane and such that a second region of the second constriction diffusion membrane is uncoupled from the first constriction diffusion membrane, the uncoupled second region defining an inflatable reservoir; and a second proliferation diffusion membrane configured to permit tissue ingrowth, the second proliferation diffusion membrane being coupled to the second constriction diffusion membrane.

According to another example, ("Example 21") further to Example 20, the first and second proliferation diffusion membranes include a plurality of small holes configured to permit tissue ingrowth and wherein the first and second constriction diffusion membranes include a plurality of small holes configured to resist tissue ingrowth.

According to another example, ("Example 22") further to any of Examples 20 to 22, the first region of the second constriction diffusion membrane is a peripheral edge region of the second constriction diffusion membrane, and wherein the first region of the second constriction diffusion membrane is coupled to a peripheral edge region of the first constriction diffusion membrane, and wherein the second region of the second constriction diffusion membrane is a region interior to the peripheral edge region of the second constriction diffusion membrane.

According to another example, ("Example 23") further to any of Examples 20 to 22, the device further includes a fluid conduit having a first end and a second end, the first end being in fluid communication with the reservoir and the second end extending away from the first and second constriction diffusion membranes and being insertable into a fluid-filled body cavity such that a fluid from the fluid-filled body cavity is transferable to the reservoir.

According to another example, ("Example 24") further to Example 23, the device further includes a third proliferation diffusion membrane including a plurality of pores sized to permit tissue ingrowth, the third proliferation diffusion membrane being situated adjacent the first proliferation diffusion membrane and extending along the fluid conduit between the first proliferation diffusion membrane and the second end of the fluid conduit.

According to another example, ("Example 25") further to Example 24, the third proliferation membrane and the first proliferation diffusion membrane are the same proliferation diffusion membrane.

According to another example, ("Example 26") further to any of Examples 24 to 25, the third proliferation diffusion membrane is coupled to the fluid conduit.

According to another example, ("Example 27") further to any of Examples 23 to 26, the device further includes a fourth proliferation diffusion membrane including a plurality of pores sized to permit tissue ingrowth, the fourth proliferation diffusion membrane being situated adjacent the second proliferation diffusion membrane and extending along the fluid conduit between the second proliferation diffusion membrane and the second end of the fluid conduit.

According to another example, ("Example 28") further to Example 27, the fourth proliferation membrane and the second proliferation diffusion membrane are the same proliferation membrane.

According to another example, ("Example 29") further to any of Examples 27 to 28, the fourth proliferation diffusion membrane includes a perforation sized to accommodate the fluid conduit such that the fluid conduit can be extended through the perforation and into the fluid-filled body cavity when implanted.

According to another example, ("Example 30") further to any of Examples 20 to 29, the fluid-filled body cavity is an anterior chamber of a patient's eye, and wherein the fluid is aqueous humor.

According to another example, ("Example 31"), a method of forming glaucoma drainage device includes providing a first proliferation diffusion membrane and a second proliferation diffusion membrane, the first and second proliferation diffusion membranes each configured to permit tissue ingrowth; providing a first constriction diffusion membrane and a second constriction diffusion membrane, the first and second constriction diffusion membranes configured to resist tissue ingrowth; and forming an aqueous humor diffusion member by coupling the first proliferation diffusion membrane to the first constriction diffusion membrane; coupling the first constriction diffusion membrane to the second constriction diffusion membrane such that a first region of a first interface surface of the second constriction diffusion membrane is coupled to the first constriction diffusion membrane and such that a second region of the first interface surface is uncoupled from the first constriction diffusion membrane, wherein the uncoupled second region defines an inflatable reservoir; and coupling the second proliferation diffusion membrane to the second constriction diffusion membrane. The method further includes coupling a fluid conduit to the aqueous humor diffusion member such that the fluid conduit is fluidly coupled with the reservoir such that the fluid conduit is operable to deliver evacuated aqueous humor to the reservoir.

According to another example, ("Example 32") further to Example 31, the aqueous humor diffusion member further comprises a third proliferation diffusion membrane configured to permit tissue ingrowth, the third proliferation membrane being situated adjacent the first proliferation diffusion membrane and extending along the fluid conduit.

According to another example, ("Example 33") further to Example 32, the aqueous humor diffusion member further comprises a fourth proliferation diffusion membrane configured to permit tissue ingrowth, the fourth proliferation membrane being situated adjacent the second proliferation diffusion membrane and extending along the fluid conduit.

According to another example, ("Example 34") further to any of Examples 31 to 33, the method further includes perforating one of the first, second, third or fourth proliferation diffusion membranes to include a plurality of pores sized to permit tissue ingrowth.

According to another example, ("Example 35") further to any of Examples 32 to 34, the third proliferation membrane and the first proliferation diffusion membrane are the same proliferation diffusion membrane.

According to another example, ("Example 36") further to any of Examples 33 to 35, the fourth proliferation membrane and the second proliferation diffusion membrane are the same proliferation diffusion membrane.

According to another example, ("Example 37") further to any of Examples 33 to 36, the fourth proliferation membrane includes a perforation sized to accommodate the fluid conduit such that the fluid conduit can be extended through the perforation and into the anterior chamber when implanted.

According to another example, ("Example 38") a biological fluid drainage device includes a body including a first microporous membrane, a second microporous membrane, and a third microporous membrane, the first microporous membrane being situated between the second and third microporous membranes, the first microporous membrane including a plurality of pores sized to resist tissue ingrowth, and the second and third microporous membranes each including a plurality of pores sized to permit tissue ingrowth, wherein an inflatable reservoir is defined between the first and third microporous membranes, wherein; and a fluid conduit having a first end and a second end, the first end being fluidly coupled with the reservoir and the second end extending outside the body and being insertable into a fluid-filled body cavity such that a fluid from the fluid-filled body cavity is transferable to the reservoir.

According to another example, ("Example 39"), further to any of the preceding examples, one or more of the first and fourth microporous membranes is hydrophobic and the second and third microporous membranes are hydrophilic.

BRIEF DESCRIPTION OF THE DRAWINGS

The accompanying drawings are included to provide a further understanding of embodiments of the disclosure and are incorporated in and constitute a part of this specification, illustrate examples, and together with the description serve to explain the principles of the disclosure.

FIG. 9A is an illustration of a glaucoma drainage device consistent with various aspects of the present disclosure.

FIG. 9B is cross sectional view of the glaucoma drainage system of FIG. 9A taken along line 9B-9B.

FIG. 9C is cross sectional view of the glaucoma drainage system of FIG. 9A taken along line 9C-9C.

DETAILED DESCRIPTION

Figure 1:
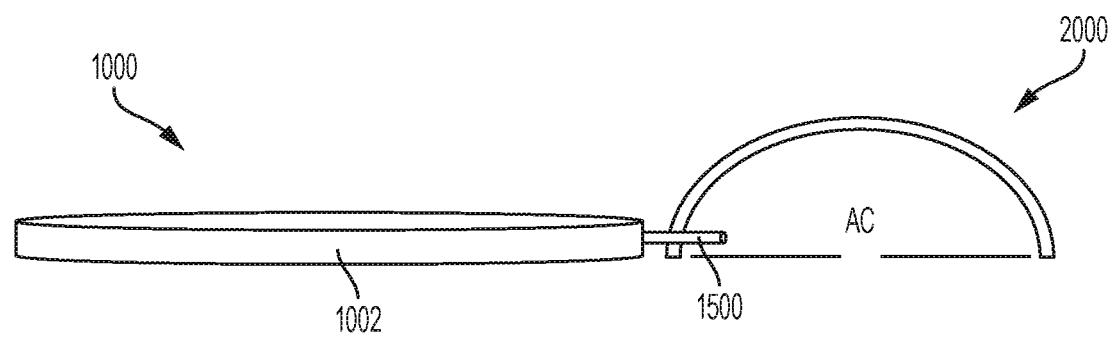
FIG. 1 is an illustration of a glaucoma drainage system consistent with various aspects of the present disclosure.

Persons skilled in the art will readily appreciate that the various embodiments of the inventive concepts provided in the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting. As used herein, the term "diffusion membranes" is meant to encompass one or more proliferation diffusion membrane and/or one or more constriction diffusion membrane.

Various aspects of the present disclosure are directed toward glaucoma drainage devices, drainage systems, and drainage methods. More specifically, the present disclosure relates to devices, systems, and methods for draining aqueous humor from the anterior chamber of a patient's eye such that it may be reabsorbed by the body. Providing a mechanism for reabsorption of the aqueous humor that has been evacuated from the anterior chamber of the eye operates to lower or otherwise stabilize the intraocular pressure.

A glaucoma drainage system 1000 according to some embodiments is illustrated in FIG. 1. The glaucoma drainage system 1000 is an implantable medical system that operates to facilitate the drainage of a fluid, such as aqueous humor, from a fluid filled body cavity, such as the anterior chamber of the eye. The glaucoma drainage system 1000 includes a fluid conduit 1500 and a body, such as an aqueous humor diffusion member 1002. While the following disclosure refers to a glaucoma drainage system 1000 for use in draining aqueous humor from the anterior chamber of the eye, it is to be understood and appreciated by one of skill in the art that the glaucoma drainage system 1000 depicted can be configured and utilized to evacuate other fluids from other fluid filled body chambers. In some examples, as explained in greater detail below, the glaucoma drainage system 1000 additionally helps facilitate reabsorption of the evacuated fluid by the body. For instance, in some embodiments, the glaucoma drainage system 1000 provides an interface between the evacuated aqueous humor and tissues, vessels and/or cells that have the ability to absorb aqueous humor and are sufficiently proximate the glaucoma drainage system 1000 to interact with the evacuated aqueous humor. Thus, in some examples, aqueous humor evacuated from the anterior chamber of the eye travels through the glaucoma drainage system 1000 before being reabsorbed by the body.

In some embodiments, when the glaucoma drainage system 1000 is implanted, aqueous humor is evacuated from the anterior chamber through the fluid conduit 1500. The evacuated aqueous humor then enters a reservoir of the aqueous humor diffusion member 1002 and percolates through one or more porous membranes of the aqueous humor diffusion member 1002, where the aqueous humor can then be reabsorbed by the body. In various embodiments, in addition to aqueous humor permeability, tissue ingrowth is permitted or promoted along one or more regions of the glaucoma drainage system 1000. For instance, the exterior of the aqueous humor diffusion member 1002 may include or be defined by one or more membranes that are porous or otherwise permeable to the fluid of the fluid filled body cavity (referred to hereinafter as diffusion membranes), and that are configured to permit or promote tissue ingrowth. Permitting tissue ingrowth along surfaces or within regions of the glaucoma drainage system 1000 helps facilitate biointegration of the glaucoma drainage system 1000 into the surrounding tissue (e.g., eye tissue), and helps facilitate reabsorption of the evacuated aqueous humor by the surrounding tissue. Moreover, biointegration including tissue ingrowth and attachment helps minimize relative movement between the glaucoma drainage system 1000 and the tissue surrounding the glaucoma drainage system 1000, which helps avoid irritation of the eye tissue that can lead to foreign body tissue response, scar formation, and/or erosion and site infection of the glaucoma drainage system 1000.

In various embodiments, the aqueous humor diffusion member 1002 includes an interior region that defines a reservoir for the aqueous humor that is evacuated from the anterior chamber through the fluid conduit 1500. The interior region of the aqueous humor diffusion member 1002 may include one or more membranes that are porous or otherwise permeable to the fluid of the fluid filled body cavity (referred to hereinafter as diffusion membranes). For example, as discussed in greater detail below, one or more of the diffusion membranes may be formed of a porous media, such as a polymeric material, that has a microstructure that is suitable for transporting fluid through a pore space of the porous media. Thus, in some embodiments, the reservoir may be defined by the pore space of one or more of the diffusion membranes that form the aqueous humor diffusion member 1002. In some embodiments, the aqueous humor diffusion member 1002 may be configured such that the reservoir is additionally or alternatively defined between two or more of the diffusion membranes that form the aqueous humor diffusion member 1002. For instance, in some embodiments, at least a portion of the surface areas between adjacently situated diffusion membranes forming the aqueous humor diffusion member 1002 remains unbonded or unadhered such that the adjacently situated diffusion membranes are operable to separate from one another along at least a portion of their surface areas to form and define the reservoir. In some embodiments, as discussed further below, the reservoir defined between adjacently situated diffusion membranes is operable to inflate or dilate in a controlled manner (e.g., to a predetermined profile when inflated) so that the glaucoma drainage system 1000 does not interfere with normal eye function (e.g., regular eye movement, including pivoting and blinking).

In various embodiments, the aqueous humor diffusion member 1002 is sized and shaped such that it is implantable within the patient's anatomy. For instance, in some embodiments, the aqueous humor diffusion member 1002 is sized and shaped such that it is implantable within a dissected subconjunctival space (e.g., between a sclera and a conjunctiva of the patient's eye). In some embodiments, the aqueous humor diffusion member 1002 is a thin, puck-shaped member. In some embodiments, the aqueous humor diffusion member 1002 has a thickness (e.g., a distance measured between the first exterior surface 1004 and the second exterior surface 1006) of less than or equal to half of a millimeter (0.5 mm), such as between one-tenth of a millimeter (0.1 mm) and half of a millimeter (0.5 mm). However, given differing anatomies of the human body, an aqueous humor diffusion member 1002 may exceed of half of a millimeter (0.5 mm) provided that the thickness does not substantially interfere with normal eye functioning (e.g., pivoting and blinking) or substantially reduce the flexibility of the aqueous humor diffusion member 1002 to the extent that undesirable relative movement occurs between the glaucoma drainage system 1000 and the surrounding tissue when implanted, resulting with a likely consequence of tissue irritation, foreign body tissue response, and/or excessive scar formation.

In some embodiments, the aqueous humor diffusion member 1002 may have a diameter in the range of five (5) millimeters to fifteen (15) millimeters, such as ten (10) millimeters for example. In some embodiments, the aqueous humor diffusion member 1002 may be ovular and include a major dimension (e.g., along a major axis of the ellipse) of up to about thirty (30) millimeters and corresponding minor dimension (e.g., along a major axis of the ellipse) of up to about ten (10) millimeters. As discussed above, given differing anatomies of the human body, an aqueous humor diffusion member 1002 may exceed such dimensions (e.g., fifteen (15), and ten (10) and thirty (30) millimeters) provided that the size does not substantially interfere with normal eye functioning (e.g., pivoting and blinking) or substantially reduce the flexibility of the aqueous humor diffusion member undesirable relative movement occurs between the glaucoma drainage system 1000 and the surrounding tissue when implanted, resulting with a likely consequence of tissue irritation, foreign body tissue response, and/or excessive scar formation. Likewise, the aqueous humor diffusion member 1002 may have a diameter of less than five (5) millimeters, three (3) millimeters, or even less than three (3) millimeters provided that the aqueous humor diffusion member 1002 is operable to accommodate a sufficient degree of evacuated aqueous humor and is operable to facilitate the reabsorption of aqueous humor to constitute an effective treatment for the patient.

In various embodiments, the fluid conduit 1500 operates to fluidly couple the reservoir with the fluid filled body cavity (e.g., the anterior chamber of the eye) when implanted in the body such that a differential pressure is achievable between the reservoir and the environment exterior to the glaucoma drainage system 1000 (e.g., atmosphere). Thus, when implanted, it is to be appreciated that a pressure within the reservoir is based, at least in part, on the pressure within the fluid filled body cavity (e.g., the Intraocular Pressure of the Anterior Chamber of the eye). In some embodiments, such a differential pressure causes the reservoir to inflate or dilate. Moreover, in some embodiments, such a differential pressure causes the aqueous humor to percolate through the diffusion membranes of the aqueous humor diffusion member 1002. That is, in some embodiments, the evacuated aqueous humor enters the reservoir and percolates through the diffusion membranes of the aqueous humor diffusion member 1002, where the aqueous humor can then be reabsorbed by the body.

Figure 2A:
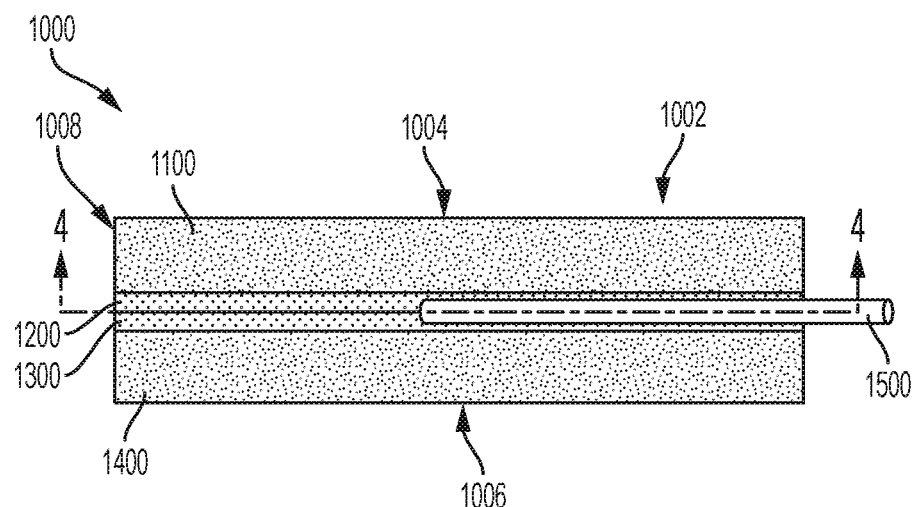
FIG. 2A is an illustration of a glaucoma drainage system in a deflated state consistent with various aspects of the present disclosure.
Figure 2B:
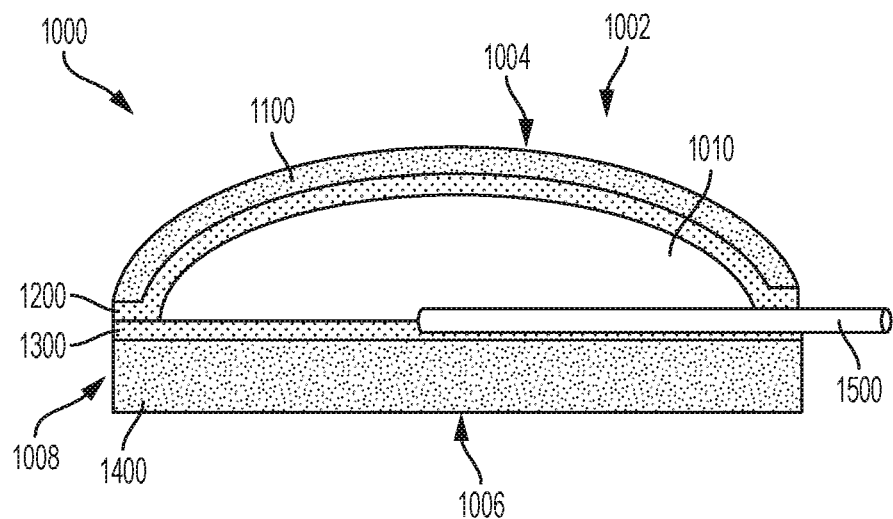
FIG. 2B is an illustration of a glaucoma drainage system in an inflated state consistent with various aspects of the present disclosure

Turning now to FIGS. 2A and 2B, a glaucoma drainage system 1000 including an aqueous humor diffusion member 1002 comprised of a plurality of diffusion membranes is shown. The aqueous humor diffusion member 1002 includes a first exterior surface 1004, a second, exterior surface 1006 opposing the first exterior surface 1004, and a periphery 1008. FIG. 2A shows the glaucoma drainage system 1000 in a deflated state. FIG. 2B shows the glaucoma drainage system 1000 in an inflated state, where aqueous humor is present within an inflatable or dilatable reservoir 1010. While the glaucoma drainage system 1000 is shown in FIG. 2B in an inflated state where the glaucoma drainage system 1000 is not uniformly inflated (e.g., the first proliferation and constriction diffusion membranes 1100 and 1200 are shown adopting a generally nonlinear configuration while the second proliferation and constriction diffusion membranes 1300 and 1400 are shown in a generally linear configuration), it is to be appreciated that the glaucoma drainage system 1000 may deform uniformly (e.g., the second proliferation and constriction diffusion membranes 1300 and 1400 may deform in a manner that mirrors the deformation of the first proliferation and constriction diffusion membranes 1100 and 1200). The aqueous humor diffusion member 1002 includes a body defined by a plurality of diffusion membranes including first and second proliferation diffusion membranes 1100 and 1400 and first and second constriction diffusion membranes 1200 and 1300. In some examples, the first and second proliferation diffusion membranes 1100 and 1400 and the first and second constriction diffusion membranes 1200 and 1300 are stacked upon one another as shown to form the aqueous humor diffusion member 1002. As discussed further below, the first and second proliferation diffusion membranes 1100 and 1400 are configured to permit tissue ingrowth and attachment, while the first and second constriction diffusion membranes 1200 and 1300 are configured to minimize, resist, or prevent tissue ingrowth and attachment.

In some embodiments, the first and second proliferation diffusion membranes 1100 and 1400 form or otherwise define an exterior of the aqueous humor diffusion member 1002, while the first and second constriction diffusion membranes 1200 and 1300 are situated between the first and second proliferation diffusion membranes 1100 and 1400 and define an interior region of the aqueous humor diffusion member 1002. In various embodiments, the first and second proliferation diffusion membranes 1100 and 1400 and the first and second constriction diffusion membranes 1200 and 1300 are each permeable to aqueous humor in that each is configured to allow evacuated aqueous humor (e.g., aqueous humor disposed within the sealed reservoir) to percolate therethrough and/or diffuse thereacross. However, the first and second proliferation diffusion membranes 1100 and 1400 are configured to permit tissue ingrowth and attachment, while the first and second constriction diffusion membranes 1200 and 1300 are configured to minimize, resist, or prevent tissue ingrowth and attachment. A configuration of constriction diffusion membranes sandwiched or otherwise situated between proliferation diffusion membranes as shown in FIGS. 2A and 2B helps to minimize, for instance, an ingress of bacteria in excess of the size of perforations or small holes present in the constriction diffusion membranes and/or migration thereof to the anterior chamber of the eye.

In various examples, the first and second proliferation diffusion membranes 1100 and 1400 of the aqueous humor diffusion member 1002 are microporous, permeable to aqueous humor, and are configured to permit the ingrowth and/or attachment of vessels and tissue. In various embodiments, the first and second constriction diffusion membranes 1200 and 1300 are also microporous and permeable to aqueous humor, but are configured to resist or otherwise minimize the ingrowth and attachment of vessels and tissue structures. Thus, in various embodiments, the aqueous humor diffusion member 1002 is formed of a plurality of distinct diffusion membranes including at least a first proliferation diffusion membrane 1100 and at least a first constriction diffusion membrane 1200.

While the glaucoma drainage system 1000 shown in FIGS. 2A and 2B includes separate and distinct first and second proliferation diffusion membranes 1100 and 1400, it is to be appreciated that the aqueous humor diffusion member 1002 may include the first proliferation diffusion membrane 1100 without also requiring a separate and distinct second proliferation diffusion membrane 1400. For instance, the first proliferation diffusion membrane 1100 may be folded such that the first proliferation diffusion membrane 1100 surrounds the constriction diffusion membrane portion (e.g., the first and/or second constriction diffusion membranes 1200 and 1300) of the aqueous humor diffusion member 1002. In some such embodiments, one or more portions of the folded portion of the proliferation diffusion membrane 1100 is bonded or welded to adjacent portions of the non-folded portion of the proliferation diffusion membrane 1200 and/or one or more portions of the constriction diffusion membrane portion of the aqueous humor diffusion member 1002. Additionally or alternatively, while the glaucoma drainage system 1000 shown in FIGS. 2A and 2B includes separate and distinct first and second constriction diffusion membranes 1200 and 1300, it is to be appreciated that the aqueous humor diffusion member 1002 may include the first constriction diffusion membrane 1200 without also requiring a separate and distinct second constriction diffusion membrane 1300. For instance, the first constriction diffusion membrane 1200 may be folded over upon itself to form a multilayered constriction diffusion membrane, wherein one or more portions of the folded portion of the constriction diffusion membrane 1200 is bonded or welded to adjacent portions of the non-folded portion of the constriction diffusion membrane 1200. Moreover, a proliferation diffusion membrane 1100 may additionally be folded about the folded constriction diffusion membrane 1200, where the constriction diffusion membrane 1200 is folded over upon itself with a fluid conduit 1500 situated between the folded and unfolded portions of the constriction diffusion membrane 1200. In some such embodiments, a reservoir may be defined between at least the folded and unfolded portions of the constriction diffusion membrane 1200.

Figure 3:
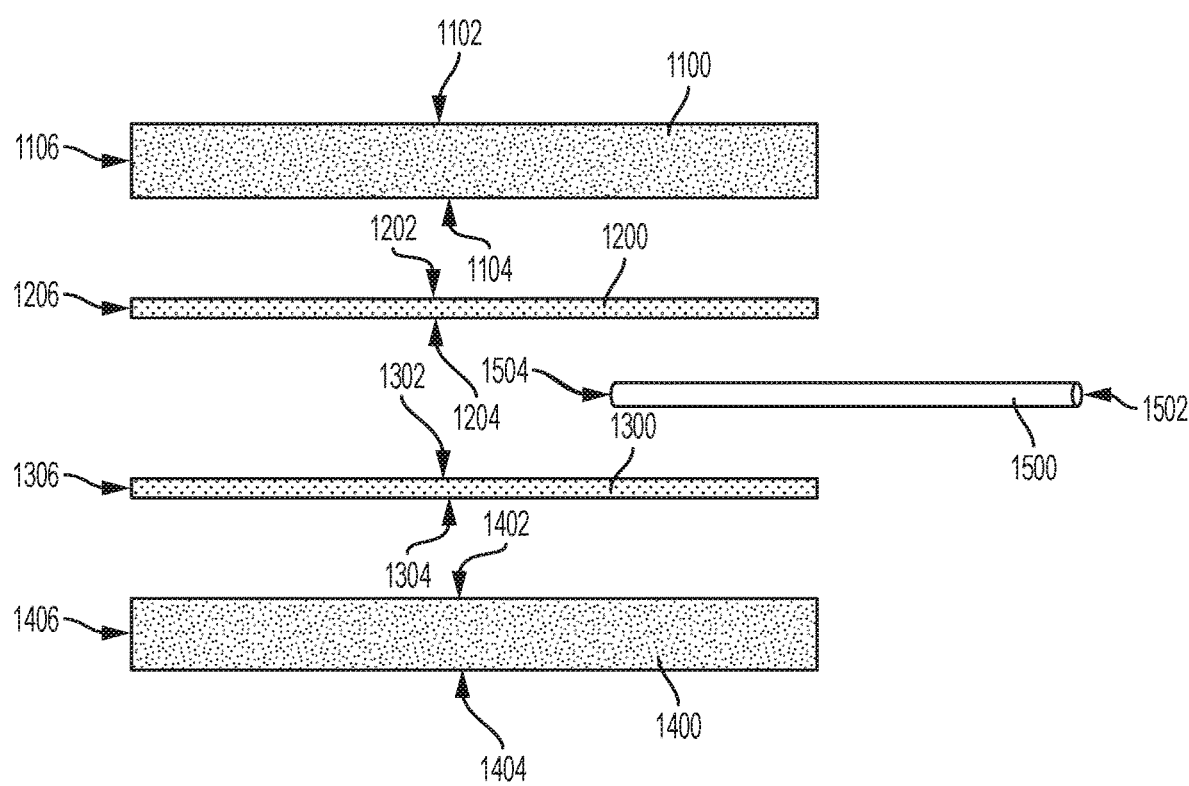
FIG. 3 is an exploded view of the glaucoma drainage system illustrated in FIG. 2.

FIG. 3 is an exploded view of the glaucoma drainage system 1000 shown in FIGS. 2A and 2B. As shown in FIG. 3, the aqueous humor diffusion member 1002 includes a body defined by a first proliferation diffusion membrane 1100, a first constriction diffusion membrane 1200, a second constriction diffusion membrane 1300, and a second proliferation diffusion membrane 1400. As shown, the various proliferation and constriction diffusion membranes each include interface surfaces and a periphery. For example, the first proliferation diffusion membrane 1100 includes a first interface surface 1102, a second interface surface 1104, and a periphery 1106. In some examples, the first interface surface 1102 of the first proliferation diffusion membrane 1100 corresponds with or otherwise defines the first exterior surface 1004 of the glaucoma drainage system 1000. Additionally, as shown in FIG. 3, first constriction diffusion membrane 1200 includes a first interface surface 1202, a second interface surface 1204, and a periphery 1206. Likewise, as shown in FIG. 3, second constriction diffusion membrane 1300 includes a first interface surface 1302, a second interface surface 1304, and a periphery 1306. As shown, the second proliferation diffusion membrane 1400 includes a first interface surface 1402, a second interface surface 1404, and a periphery 1406. In some examples, the second interface surface 1404 of the second proliferation diffusion membrane 1400 corresponds with or otherwise defines the second exterior surface 1006 of the glaucoma drainage system 1000.

In various embodiments, the diffusion membranes (i.e., the proliferation diffusion membranes and the constriction diffusion membranes) forming the aqueous humor diffusion member 1002 are situated adjacent to one another in a stacked configuration. For example, as illustrated in FIGS. 2A, 2B, and 3, the first and second proliferation diffusion membranes 1100 and 1400 and first and second constriction diffusion membranes 1200 and 1300 are situated adjacent to one another in a stacked configuration, with the first and second proliferation diffusion membranes 1100 and 1400 forming or otherwise defining an exterior of the aqueous humor diffusion member 1002, and with the first and second constriction diffusion membranes 1200 and 1300 sandwiched or otherwise situated between the first and second proliferation diffusion membranes 1100 and 1400. Thus, the proliferation diffusion membranes forming the exterior region of the aqueous humor diffusion member 1002 are configured to support or permit tissue ingrowth and attachment, while the constriction diffusion membranes forming the interior region of the aqueous humor diffusion member 1002 are configured to minimize, resist, or prevent tissue ingrowth and attachment beyond or interior to a boundary or interface between the proliferation and constriction diffusion membranes.

By minimizing, resisting, or preventing tissue ingrowth and attachment beyond or interior to the constriction diffusion membranes, the glaucoma drainage system 1000 minimizes, resists, or prevents tissue ingrowth into the reservoir 1010, which helps maintain performance of the glaucoma drainage system 1000 during and after biointegration thereof. For example, it is to be appreciated that minimizing, resisting, or preventing tissue ingrowth into the constriction diffusion membranes, and thus the reservoir 1010 operates to maintain a flexibility of the glaucoma drainage system 1000, which as discussed herein helps minimize relative movement between the glaucoma drainage system 1000 and the surrounding tissue and thus helps minimize irritation of the surrounding tissue. In particular, minimizing, resisting, or preventing tissue ingrowth into the constriction diffusion membranes helps avoid tissue from proliferating across the interface between adjacent constriction diffusion membranes an thus helps avoid such tissue ingrowth from interlocking the constriction diffusion membranes together. Avoiding the interlocking the constriction diffusion membranes helps maintain the ability of the constriction diffusion membranes to slide and move relative to one another, which helps maintain flexibility of the glaucoma drainage system 1000.

In some examples, as discussed further below, the aqueous humor diffusion membrane 1002 is configured such that the interface surfaces of adjacently situated diffusion membranes face one another. In some examples, the first and second proliferation diffusion membranes 1100 and 1400 and the first and second constriction diffusion membranes 1200 and 1300 are oriented such that their peripheries align with and/or are coaxial with one another. In some embodiments, one or more of the peripheries of the diffusion members forming the body of the aqueous humor diffusion member 1002 form the periphery 1008 of the aqueous humor diffusion member 1002. For example, as shown in FIGS. 2A and 2B, the peripheries 1106, 1206, 1306, and 1406, collectively, form or define the periphery 1008 of the aqueous humor diffusion member 1002. It is to be appreciated, however, that the periphery of the aqueous humor diffusion member 1002 may be formed from less than all of the peripheries of the diffusion membranes forming the body of the aqueous humor diffusion member 1002. For instance, in some examples, the periphery 1008 of the aqueous humor diffusion member 1002 may be formed or defined by the peripheries 1106 and 1406 of the first and second proliferation diffusion membranes 1100 and 1400.

As mentioned above, in various embodiments, adjacently situated diffusion membranes are generally oriented such that one or more of their interface surfaces is situated adjacent to or otherwise faces an interface surface of an adjacently situated diffusion membrane. That is, in various embodiments, the interface surfaces of adjacently situated diffusion membranes face each other. In the embodiment depicted in FIGS. 2A, 2B, and 3, the first proliferation diffusion membrane 1100 and the first constriction diffusion membrane 1200 are adjacently situated such that the second interface surface 1104 of first proliferation diffusion membrane 1100 faces the first interface surface 1202 of first constriction diffusion membrane 1200. Similarly, as shown in FIGS. 2A, 2B, and 3, first constriction diffusion membrane 1200 and second constriction diffusion membrane 1300 are adjacently situated such that the second interface surface 1204 of first constriction diffusion membrane 1200 faces the first interface surface 1302 of second constriction diffusion membrane 1300. Similarly, as shown in FIGS. 2A, 2B, and 3, second constriction diffusion membrane 1300 and second proliferation diffusion membrane 1400 are adjacently situated such that the second interface surface 1304 of second constriction diffusion membrane 1300 faces the first interface surface 1402 of second proliferation diffusion membrane 1400.

Thus, in some embodiments, stacked configurations like those described above provide for a first diffusion membrane having first and second interface surfaces and a second diffusion membrane having first and second interface surfaces where the first and second diffusion membranes are adjacently situated such that the second interface surface of the first diffusion membrane faces the first interface surface of the second diffusion membrane.

In various embodiments, the first and second proliferation diffusion membranes 1100 and 1400 and the first and second constriction diffusion membranes 1200 and 1300 may include or be formed of one or more layers or sheets of expanded polytetrafluoroethylene (ePTFE), or other polymers, such as, but not limited, to polyurethane, polysulfone, polyvinylidene fluorine (PVDF), polyhexafluoropropylene (PHFP), perfluoroalkoxy polymer (PFA), polyolefin, fluorinated ethylene propylene (FEP), acrylic copolymers and other suitable fluoro-copolymers. These polymers can be in sheet, knitted or woven (including individual or multi-fiber strands), or non-woven porous forms. In some examples, one or more of the first and second proliferation diffusion membranes 1100 and 1400 and/or the first and second constriction diffusion membranes 1200 and 1300 may be formed from a plurality of layers or sheets of polymer material. In some such examples, the layers or sheets of polymer material may be laminated or otherwise mechanically coupled together, such as by way of heat treatment and/or high pressure compression and/or adhesives and/or other lamination methods known by those of skill in the art. In some embodiments, as explained in greater detail below, the layers of polymer material may be coupled together at discrete locations to form stabilizing structures that extend through the resulting proliferation and/or constriction diffusion membranes. Similarly, in some embodiments, as explained in greater detail below, proliferation and/or constriction diffusion membranes may be coupled together at discrete locations to form stabilizing structures that extend through the resulting aqueous humor diffusion member 1002. It is to be appreciated that such stabilizing structures are operable to constrain a shape or profile of the aqueous humor diffusion member 1002 upon inflation or dilation of the reservoir 1010, as mentioned above.

In some embodiments, the layers or sheets of polymer material forming the first and/or second proliferation diffusion membranes 1100 and 1400 and/or the first and/or second constriction diffusion membranes 1200 and 1300 may be subjected to one or more processes prior to or after their formation to modify their microstructure (and thus their material properties) to increase or decrease a natural permeability (e.g., a permeability to aqueous humor) of the polymeric material(s). In some examples, such processes include, but are not limited to, material coating processes, surface preconditioning processes, and/or perforation processes. Material coating processes may be utilized to at least partially fill the porous space of the polymeric material(s), to thereby reduce permeability, as those of skill will appreciate. Additionally or alternatively, material coating processes may be utilized to apply one or more drug or antimicrobial coatings to the surface of the polymer material (such as metallic salts, including silver carbonate), and organic compounds (e.g. chlorhexidine diacetate), to the polymer material.

In some embodiments, one or both of the first and second proliferation diffusion membranes 1100 and 1400 and/or one or both of the first and second constriction diffusion membranes 1200 and 1300 may be hydrophilic. In some embodiments, one or both of the first and second proliferation diffusion membranes 1100 and 1400 and/or one or both of the first and second constriction diffusion membranes 1200 and 1300 is hydrophobic. Thus, in some examples, the aqueous humor diffusion member 1002 may include one or more hydrophilic membranes, and one or more hydrophobic membranes.

Accordingly, hydrophilic coatings to enable wet out of the polymer matrix may also be applied as if the polymer surfaces are hydrophobic in nature. Surface coatings comprising antioxidant components can be applied to mitigate the body's inflammatory response that naturally occurs during wound healing after surgery. Surfaces can be modified with anti-proliferative compounds (e.g. Mitomycin C, 5-fluoracil), to moderate the surrounding tissue response in the eye. In some examples, one or more surface preconditioning processes may additionally or alternatively be utilized to form layers exhibiting a preferred microstructure (e.g., wrinkles, folds, or other geometric out-of-plane structures), as explained in U.S. Pat. No. 9,849,629 to Zagl, et al. Such surface preconditioning could facilitate a bolder early inflammatory phase after surgery, providing an early stable interface between porous device and tissue. In some examples, a heparin coating (e.g., thromboresistant) may additionally or alternatively be applied to help minimize or reduce cell formation including fibrinogen buildup following a surgical implantation procedure.

In some embodiments, one or more perforation processes may additionally or alternatively be utilized to form a plurality of perforations or small holes in the polymeric material(s) in addition to any perforations or small holes naturally occurring in the polymeric material(s), which operates to increase a natural permeability (e.g., a permeability to aqueous humor) of the polymeric material(s). Such perforation processes may increase a number of perforations or small holes present in the polymeric material(s) and/or may increase an average size of the perforations or small holes present in the polymeric material(s), and may be performed before and/or after the formation of the proliferation and/or constriction diffusion membranes. In some embodiments, the permeability of the first and/or second proliferation diffusion membranes 1100 and 1400 and/or the first and second constriction diffusion membranes 1200 and 1300 may be altered to tune or otherwise modify flux and/or flow resistance of aqueous humor to a desired amount.

In various embodiments, the first and/or second proliferation diffusion membranes 1100 and 1400 may include perforations or small holes that range in size (or average size) from between twenty (20) microns and one-hundred (100) microns. In other examples, the size (or average size) of the perforations or small holes in the first and/or second proliferation diffusion membranes 1100 and 1400 may exceed one-hundred-fifty (150) microns. In various embodiments, the first and/or second proliferation diffusion membranes 1100 and 1400 may include perforations or small holes less than twenty (20) microns, but larger than one (1) or two (2) microns, as perforations or small holes less than one (1) or two (2) microns generally inhibit, resist, or otherwise prevent ingrowth of vessels and other tissues.

Accordingly, in various embodiments, the first and second constriction diffusion membranes 1200 and 1300 are configured or selected such that the perforations or small holes therein are generally sized at less than (or have an average size of less than) one (1) micron or two (2) microns to minimize, resist, or prevent the ingrowth and attachment of tissue, while maintaining aqueous humor permeability.

It is to be appreciated that the first and second proliferation diffusion membranes 1100 and 1400 may be configured to have the same or different permeabilities. Similarly, it is to be appreciated that the first and second constriction diffusion membranes 1200 and 1300 may be configured to have the same or different permeabilities. In some examples, the various proliferation and constriction diffusion membranes discussed herein may possess the same inherent permeabilities, but undergo one or more of the material modification processes discussed herein to achieve different relative permeabilities. In some embodiments, one or more of the material modification processes discussed herein operates to change or otherwise modify the naturally occurring permeability of the polymeric material(s). Thus, in some embodiments, the permeabilities of the proliferation and/or constriction diffusion membranes may be based on the naturally occurring microstructure of the polymeric material(s) and/or one or more of the material modification processes discussed herein. Those of skill in the art will appreciate that a permeability is generally related to the resistance of a fluid transporting through the pore space of porous media, and that materials associated with low permeabilities exhibit greater resistance to flow than do those materials with higher permeability.

In some embodiments, the perforations or small holes in the proliferation and constriction diffusion membranes may be formed through one or more salt inclusion processes, or through the use of one or more drilling, die-punching, needle-puncturing, or laser cutting processes, which may be performed before and/or after the formation of the proliferation and/or constriction diffusion membranes.

Generally, the processes described above may be utilized to form proliferation diffusion membranes having a microstructure that permits the ingrowth of surrounding vessels and other tissues and that is permeable to aqueous humor. Similarly, the processes described above may be utilized to form constriction diffusion membranes having a microstructure that minimizes, resists, or otherwise prevents the ingrowth of surrounding vessels and other tissues, but that is permeable to aqueous humor. The aqueous humor that percolates and/or diffuses across the constriction and proliferation diffusion membranes may be absorbed by the vessels that have grown into the proliferation diffusion membranes and/or the vessels exterior to the aqueous humor diffusion member 1002, and/or may percolate through the surrounding tissues and into the tear film.

As mentioned above, in some embodiments, the differential pressure observed between the reservoir 1010 of the glaucoma drainage system 1000 and the environment exterior to the glaucoma drainage system 1000 (e.g., atmospheric pressure) is a mechanism that facilitates the flow of aqueous humor through the aqueous humor diffusion member 1002 of the glaucoma drainage system 1000. In some embodiments, the mechanism of reabsorption and the carrying away of the evacuated aqueous humor by the vessels grown into and surrounding the glaucoma drainage system 1000 helps facilitate the evacuation of aqueous humor from the anterior chamber.

However, it is to be appreciated that in addition to facilitating the reabsorption and carrying away of evacuated aqueous humor, the ingrowth of tissues, vessels, and cells into the proliferation diffusion membrane(s) of the aqueous humor diffusion member 1002 also helps prevent, reduce, minimize, or limit the onset of foreign body tissue responses. Specifically, as mentioned above tissue ingrowth and attachment helps minimize relative movement between the glaucoma drainage system 1000 and the tissue of the eye. By helping minimize such relative movement, the glaucoma drainage system 1000 helps avoid irritation of the eye tissue that can occur and that can lead to foreign body tissue response, which can lead to excessive scar formation and/or erosion and site infection of the glaucoma drainage system 1000.

In some embodiments, one or more of the adjacently situated diffusion membranes forming the body of the aqueous humor diffusion member 1002 are connected or otherwise coupled to together. In some embodiments, adjacently situated diffusion membranes are coupled at one or more discrete portions or regions along their adjacently facing interface surfaces. In some embodiments, adjacently situated diffusion membranes may be coupled along at least a portion of an adjoining edge (or edges). In other embodiments, adjacently situated diffusion membranes may be additionally or alternatively coupled at one or more discrete location along the adjoining surfaces interior to the edge (or edges). In yet other embodiments, adjacently situated diffusion membranes may be coupled along an entirety of their adjacently facing interface surfaces (e.g., applying an adhesive across an entirety of a surface area of adjacently facing interface surfaces). Thus, in some embodiments, one or more of the adjacently situated diffusion membranes may be coupled at less than all of their adjacently facing interface surfaces (e.g., at discrete locations or a portion thereof) or they may be coupled along an entirety of the facing interface surfaces.

In those embodiments where adjacently situated diffusion membranes are coupled along a portion of less than all of their adjacently facing interface surfaces, one or more discrete locations along adjacently facing interface surfaces are connected or otherwise coupled together while one or more other discrete locations along adjacently facing interface surfaces are not coupled together. That is, in some embodiments, at least one region or area of adjacently facing interface surfaces remains intentionally unadhered, unbonded, or otherwise uncoupled.

In some such embodiments, these uncoupled regions or areas may include regions or areas central to a peripheral edge. Generally, these uncoupled regions or areas are free to move or slide relative to one another, and may separate from one another to serve as a reservoir for the accumulation of evacuated aqueous humor. In various examples, providing such a degree of freedom (e.g., in shear) provides for considerable flexibility because diffusion membranes can move relative to one another to conform to changes in curvature as the aqueous humor diffusion member 1002 is bent and moves, such as with natural movement of the eye. Thus, the discontinuity of coupling of the diffusion membranes provides for a glaucoma drainage system 1000 exhibiting better eye conformity and that is better suited to dynamically respond to changes in curvature of the eye 2000 as the patient blinks, focuses, and moves the eye within the eye socket. Unlike the more rigid conventional designs, the increased flexibility also minimizes movement of the glaucoma drainage system 1000 relative to the surrounding tissue.

Figure 4A:
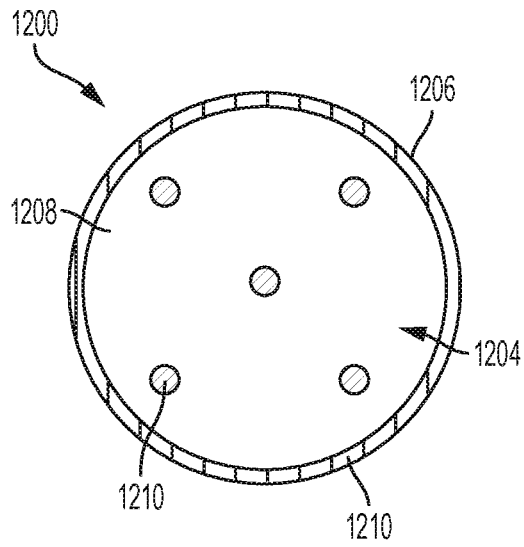
FIGS. 4A-4D are illustrations of constriction diffusion membrane interface surfaces consistent with various aspects of the present disclosure.

Turning now to FIGS. 4A to 4D, examples of interface surfaces including coupled and uncoupled (e.g., bonded and unbonded) regions are illustrated. FIG. 4A is a cross sectional view of second interface surface 1204 taken along the boundary (4-4, FIG. 2) situated between adjacently facing first and second interface surfaces 1204 and 1302, and with fluid conduit 1500 removed for clarity. As mentioned above, in some embodiments, adjacently facing interface surfaces may be coupled together at a plurality of discrete locations such that adjacently facing interface surfaces include coupled regions and uncoupled regions. FIG. 4A shows second interface surface 1204 of first constriction diffusion membrane 1200, which includes coupled regions 1210 (illustrated as cross-hatched regions) where the second interface surface 1204 is coupled to adjacently facing first interface surface 1302 of second constriction diffusion membrane 1300 in addition to a coupling along the peripheral edge 1206. As shown in FIG. 4A, second interface surface 1204 of first constriction diffusion membrane 1200 also includes uncoupled regions 1208 (illustrated as regions between and around the cross-hatched regions) where the second interface surface 1204 is situated adjacent to but otherwise uncoupled from adjacently facing first interface surface 1302 of second constriction diffusion membrane 1300. In this illustrated example of FIG. 4A, adjacently facing first and second interface surfaces 1204 and 1302 are free to slide and move relative to one another along uncoupled regions 1208. Moreover, these uncoupled regions 1208 are free to separate from one another to form the reservoir 1010 for the accumulation of aqueous humor.

It will be appreciated that while the uncoupled regions 1208 between the first and second constriction diffusion membranes 1200 and 1300 shown in FIGS. 4A to 4D are free to separate from one another to form the reservoir 1010, the coupled regions 1210 are configured to remain coupled. In various examples, these coupled regions 1210 operate to control the profile of the glaucoma drainages system 1000 as the reservoir 1010 inflates or dilates.

Figure 4B:
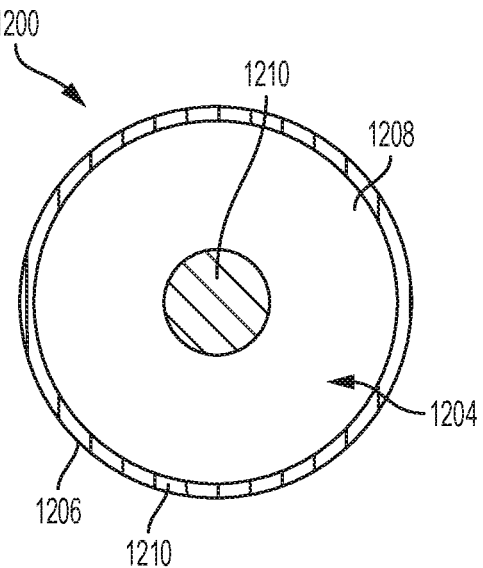

FIG. 4B is a cross sectional view of second interface surface 1204 taken along the boundary (4-4, FIG. 2) situated between adjacently facing first and second interface surfaces 1204 and 1302. FIG. 4B illustrates an another configuration where second interface surface 1204 includes a centrally positioned coupled region 1210 (illustrated as cross-hatched regions) where second interface surface 1204 is coupled to adjacently facing first interface surface 1302 of second constriction diffusion membrane 1300 in addition to being coupled along the peripheral edge 1206. Though not illustrated, it is to be appreciated that the coupling configurations of FIGS. 4B and 4A may be combinable in-whole or in-part.

Figure 4C:
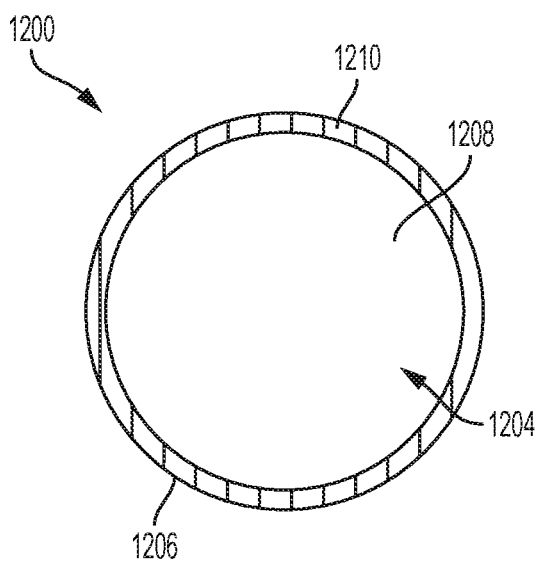

FIG. 4C illustrates another configuration where second interface surface 1204 includes a peripherally positioned coupled region 1210 (illustrated as a cross-hatched region) while second interface surface 1204 is coupled to adjacently facing first interface surface 1302 of second constriction diffusion membrane 1300. Though not illustrated, it should be appreciated that the coupling configurations of FIGS. 4C, 4B, and/or 4A may be combinable in-whole or in-part.

Figure 4D:
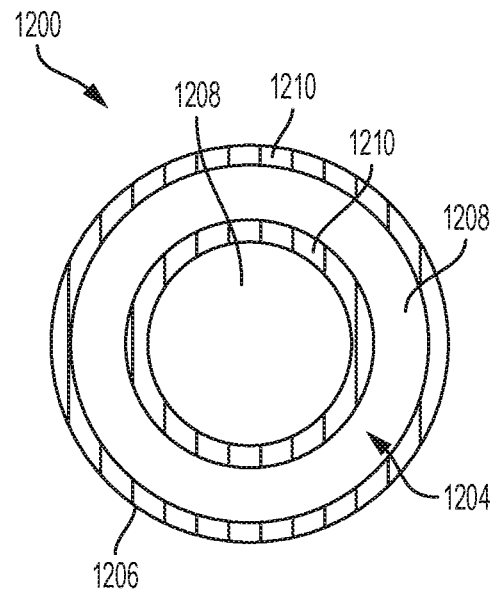

FIG. 4D illustrates another alternative configuration where second interface surface 1204 includes a peripherally positioned coupled region 1210 and a concentric annular inner coupled region 1210 (both illustrated as cross-hatched regions) where second interface surface 1204 is coupled to adjacently facing first interface surface 1302 of second constriction diffusion membrane 1300. The configuration shown in FIG. 4D in one that includes a possibility of two distinct reservoirs for the accumulation of aqueous humor. The first reservoir corresponds to the uncoupled portion 1208 radially inwardly of the concentric annular inner coupled region 1210 radially inwardly of the peripherally positioned coupled region 1210 about the periphery 1206. The second reservoir corresponds to the uncoupled portion 1208 situated between the concentric annular inner coupled region 1210 and the peripherally positioned coupled region 1210. It is to be appreciated that a first fluid conduit may be fluidly coupled with the first reservoir while a second fluid conduit is coupled with the second reservoir of the configuration shown in FIG. 4D. Alternatively, a single fluid conduit may be fluidly coupled with both of the first and second reservoirs shown in FIG. 4D, such as by way of corresponding apertures in the fluid conduit. In another alternative example, a portion of less than all of the concentric annular inner coupled region 1210 may alternatively be uncoupled such that the first and second reservoir are fluidly coupled. While not illustrated, it should be appreciated that the coupling configurations of FIGS. 4D, 4C, 4B, and/or 4A may be combinable in-whole or in-part.

It should also be appreciated that while FIGS. 4A-4D illustrate exemplary coupled and uncoupled (e.g., bonded and unbonded) regions of second interface surface 1204, adjacently facing first interface surface 1302 includes coupled and uncoupled regions corresponding to those coupled and uncoupled regions, respectively, of second interface surface 1204. Additionally, it should be appreciated that the illustrated embodiments of FIGS. 4A-4D should not be interpreted as limiting the disclosure to the illustrated embodiments. Instead, those of skill in the art will appreciate that virtually any pattern of coupled and uncoupled regions may be utilized without departing from the spirit or scope of the disclosure.

Though the boundary between first proliferation diffusion membrane 1100 and first constriction diffusion membrane 1200 is not illustrated, it should be appreciated that adjacently facing first and second interface surfaces 1202 and 1104 may be uniformly coupled across the entire boundary or alternatively coupled according to the above-discussed embodiments. Likewise, though the boundary between second proliferation diffusion membrane 1400 and second constriction diffusion membrane 1300 is not illustrated, it should be appreciated that adjacently facing first and second interface surfaces 1402 and 1304 may be uniformly coupled across the entire boundary or alternatively coupled according to the above-discussed embodiments.

As previously discussed, adjacent diffusion membranes may be connected or coupled to one another by way of one or more heat treatment processes and/or one or more bonding agents such as one or more adhesives. In some embodiments, adjacently situated diffusion membranes and/or the layers of material forming a diffusion membrane, are partially or completely bonded via thermal methods when each of the materials are brought to or above their melting temperatures. In some embodiments, such thermal processes facilitate adhesive or cohesive bond formation between the polymer materials or layers of polymeric material. In some embodiments, adjacently situated diffusion membranes forming a diffusion membrane, are partially or completely bonded via thermal methods when at least one of the materials is brought to or above its melting temperature. In some embodiments, such thermal processes facilitate adhesive or cohesive bond formation between the materials or layers of material. In some embodiments, one or more suitable adhesives are utilized and provide a sufficiently bonded interface, which can be continuous or discontinuous.

As discussed above, in various embodiments, the glaucoma drainage system 1000 is operable or otherwise configured to evacuate aqueous humor from the anterior chamber (AC) of the eye. In some embodiments, the glaucoma drainage system 1000 includes a fluid conduit 1500, as shown in at least FIG. 1. In various embodiments, fluid conduit 1500 is a compliant tubular structure (e.g., a catheter) that extends into an interior of the aqueous humor diffusion member 1002 and fluidly couples the aqueous humor diffusion member 1002 and the anterior chamber of the eye. The fluid conduit 1500 provides fluid egress from the anterior chamber. As shown in FIG. 3, the fluid conduit 1500 includes a first end 1502 and a second end 1504, and lumen extending from the first end 1502 to the second end 1504. Generally, the fluid conduit 1500 may be formed from silicone, ePTFE, polycarbonate, polyethylene, polyurethane, polysulfone, PVDF, PHFP, PFA, polyolefin, FEP, acrylic copolymers and other suitable fluoro-copolymers, alone or in combination or any other biocompatible polymer suitable for forming a compliant fluid conduit 1500.

In some embodiments, the fluid conduit 1500 is formed via a tubular melt extrusion process. In some embodiments, an extruded fluid conduit 1500 may be drawn down to a final target dimension. In some embodiments, the fluid conduit 1500 is formed via a tube paste-extrusion and expansion process commensurate with producing a desired wall thickness, porosity, stiffness, and/or dimension. In some embodiments, the fluid conduit 1500 is formed via one or more tape wrapping processes where a tape is wrapped around a mandrel of a designated dimension and cross-section. In some embodiments, the wound tape may further be bonded to itself via one or more thermal or adhesive methods before or after removal from the mandrel. In various embodiments, a wrapped tape configuration (e.g., ePTFE) provides for a fluid conduit 1500 construction having different layers with differing porosities. For example, an inner wound layer may be more porous than an outer wound layer. In some embodiments, the fluid conduit 1500 is formed via successive dip-coating of a material onto a properly-sized mandrel followed by solvent removal and mandrel extraction from the formed fluid conduit 1500.

In some embodiments, a diameter of lumen of the fluid conduit 1500 is one that is sufficient to allow flow of aqueous humor through the fluid conduit 1500 from the anterior chamber to the aqueous humor diffusion member 1002, but that does not result in a fluid conduit 1500 having an exterior diameter that significantly interferes with or impairs normal eye functions (e.g., does not interfere with blinking or regular eye movement).

As mentioned above, the fluid conduit 1500 fluidly couples the aqueous humor diffusion member 1002 to the anterior chamber of the eye such that aqueous humor can be evacuated from the anterior chamber and delivered to the aqueous humor diffusion member 1002, and in particular to the reservoir defined within the interior region of the aqueous humor diffusion member 1002. Accordingly, the fluid conduit 1500 is configured to extend between the anterior chamber of the eye and the position on the eye at which the aqueous humor diffusion member 1002 is mounted or otherwise integrated. In some embodiments, a length of the fluid conduit 1500 may be between one (1) millimeter and thirty (30) millimeters, though generally the length of the fluid conduit 1500 is oversized (or otherwise longer than necessary) such that a physician may trim its length to a specific length required for the unique anatomy of the patient. However, in various embodiments, the length and diameter of the lumen of the fluid conduit 1500 are preselected to control pressure drop across the length to minimize the risk of hypotony (e.g. dangerously low of eye pressure), as the pressure drop across the fluid conduit 1500 is a function of the length of the fluid conduit 1500. In some embodiments, the fluid conduit 1500 may be premarked with cutoff length identifiers that correspond to theoretically expected pressure drops when implanted. Such a configuration provides the physician with an option for specifically tailoring the pressure drop to the patient's particular needs. In such embodiments, after trimming the fluid conduit 1500 to the length corresponding to the desired pressure drop, the physician may optionally advance the first end 1502 of the fluid conduit 1500 further into the anterior chamber or alternatively position the aqueous humor diffusion member 1002 further from the point of penetration of the fluid conduit 1500 into the anterior chamber (e.g., further around the eye) to accommodate a desired length.

In various embodiments, the fluid conduit 1500 may be porous or non-porous, or may include a combination of porous portions and non-porous portions. For instance, in some embodiments, the fluid conduit 1500 may have a length defined by a first portion (or region) and a second portion (or region). In some embodiments, the first portion may be a non-porous portion while the second portion is a porous portion. In some embodiments, the non-porous portion is impermeable to aqueous humor while the porous portion is permeable to aqueous humor. Thus, in some embodiments, aqueous humor evacuated from the anterior chamber by the fluid conduit 1500 may percolate through the porous portion of the fluid conduit 1500. For example, the portion of the fluid conduit 1500 in the anterior chamber may have an outer surface that is impermeable to aqueous humor or cellular penetration, while a portion of the fluid conduit 1500 outside the anterior chamber may permit or otherwise allow cellular infiltration and tissue ingrowth and biointegration. In some embodiments, an inner surface of the fluid conduit 1500 may be impermeable to aqueous humor and is configured to minimize the ingress of bacteria and the ingrowth of vessels and tissue structures.

In some embodiments, the porous portion of the fluid conduit 1500 may be formed by subjecting one region (e.g., a portion of the length of the fluid conduit 1500) to one or more of the perforation processes discussed above to form a plurality of perforations in the subjected region. However, the fluid conduit 1500 need not include a portion that is permeable to aqueous humor.

Generally, the flow of aqueous humor through the glaucoma drainage system 1000 is governed by a pressure difference between the intraocular pressure and the pressure within the aqueous humor diffusion member 1002 (e.g., which is a function of the forces acting on the aqueous humor diffusion member 1002, such as atmospheric pressure). A pressure difference between these pressure regions will cause aqueous humor to flow from the anterior chamber to the glaucoma drainage system 1000. In some embodiments, the rate at which the aqueous humor flows through the glaucoma drainage system 1000 is governed by this pressure difference and a resistance to flow. In some embodiments, the resistance to flow is a function of fluid conduit flux resistance (e.g., based on tube geometry, diameter, and length, generally based on the Hagen-Poiseuille Equation) and a flux resistance of the aqueous humor through the aqueous humor diffusion member 1002, as those of skill will appreciate. In some embodiments, as mentioned above, a flux resistance of the aqueous humor through the aqueous humor diffusion member 1002 can be controlled through a permeability of the underlying materials forming the aqueous humor diffusion member 1002.

As mentioned above, the fluid conduit 1500 is a soft and compliant biocompatible tubular structure. In some embodiments, the fluid conduit 1500 is compliant in that it exhibits low column strength and is generally incapable of supporting its own weight. That is, in some embodiments, the fluid conduit 1500 lacks a sufficient amount of structural integrity (e.g. compressive hoop strength) necessary to avoid collapsing (e.g., a collapse of the inner lumen extending through the fluid conduit 1500) under its own weight.

In some embodiments, the intraocular pressure of the anterior chamber inflates or otherwise operates to maintain the generally tubular geometry (e.g., avoid collapse of the inner lumen 1506A) of the fluid conduit 1500. That is, in some embodiments, the aqueous humor flowing through the lumen of the fluid conduit 1500 operates to inflate the lumen. Such a configuration provides for a soft and compliant fluid conduit 1500 that conforms to the curvature of the eye and avoids interfering with normal eye function (e.g., pivoting and blinking). It is to be appreciated that, in some embodiments, the fluid conduit 1500 may alternatively be constructed such that it exhibits a sufficient amount of structural integrity to maintain its generally tubular geometry and/or avoid a collapse of the inner lumen.

Referring again to FIG. 3, in some embodiments, the fluid conduit 1500 includes a first end 1502 and an opposing second end 1504. In some embodiments (not illustrated in FIG. 3), the fluid conduit 1500 includes a lumen extending from the first end 1502 to the second end 1504. In some embodiments, the first end 1502 is insertable into the anterior chamber and the second end 1504 inserted into or otherwise attached to the aqueous humor diffusion member 1002. In some embodiments, the first end 1502 is positionable within the anterior chamber such that the first end 1502 extends into an interior region of the anterior chamber.

In some embodiments, after placing the first end 1502 of the fluid conduit 1500 into the anterior chamber, the fluid conduit 1500 may be secured to avoid dislodgement of the fluid conduit 1500 from within the anterior chamber. In some embodiments, one or more stitches are utilized to couple the fluid conduit 1500 and/or the aqueous humor diffusion member 1002 to the eye tissue. In some embodiments, a biocompatible tissue adhesive is used to bond the fluid conduit 1500 and/or the aqueous humor diffusion member 1002 to surrounding or adjacent tissue. In some embodiments, a needle track that is created through tissue prior to placement of the fluid conduit 1500 can be sized so as to provide a sufficient interface fit with the fluid conduit 1500 over the length of the needle-tract. In some embodiments, the first end 1502 of the fluid conduit 1500 can additionally or alternatively be flared to a greater diameter than other portions (e.g., a central portion) of the fluid conduit 1500 (or a lumen in the tissue through which the fluid conduit 1500 extends) to create an interference attachment that helps to maintain placement of the first end 1502 within the anterior chamber of the eye. In some examples, the flared first end 1502 of the fluid conduit 1500 helps avoid dislodgment of the fluid conduit 1500 from it position within the anterior chamber.

Figure 5:
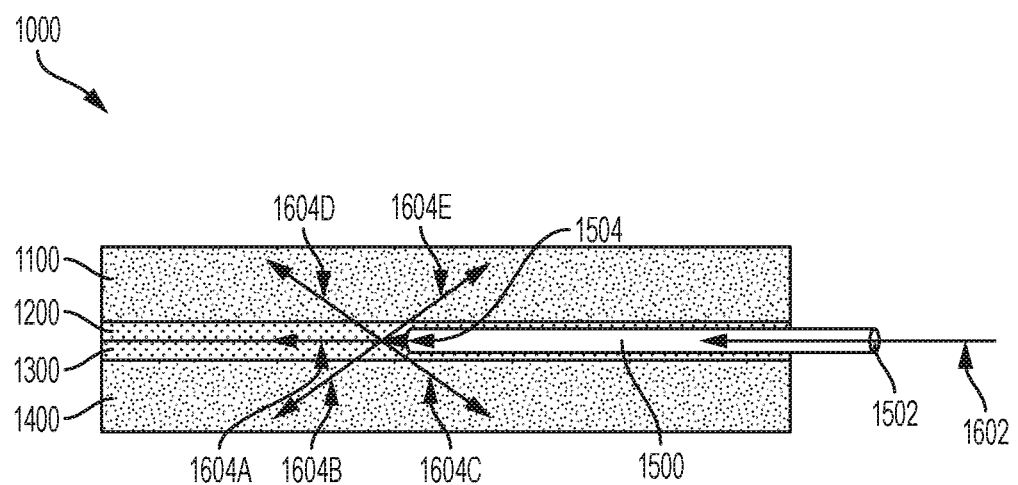
FIG. 5 is an illustration of a glaucoma drainage system consistent with various aspects of the present disclosure.

In some embodiments, the second end 1504 of the fluid conduit 1500 is coupled with the aqueous humor diffusion member 1002 such that the reservoir defined within the aqueous humor diffusion member 1002 is fluidly coupled with the fluid conduit 1500, and thus the fluid filled body cavity (e.g., the anterior chamber of the eye) when the glaucoma drainage system 1000 is implanted within the body. In some embodiments, the second end 1504 of the fluid conduit 1500 extends into or otherwise terminates within the interior of the aqueous humor diffusion member 1002, such as between the first and second constriction diffusion membranes 1200 and 1300 defining the reservoir. For example, as shown in FIG. 5, the fluid conduit 1500 is coupled to the aqueous humor diffusion member 1002 such that the fluid conduit 1500 terminates within an interior of the aqueous humor diffusion member 1002. That is, in some embodiments, the second end 1504 is coupled to the aqueous humor diffusion member 1002 such that evacuated aqueous humor exiting the fluid conduit 1500 at the second end 1504 diffuses or is otherwise injected into the aqueous humor diffusion member 1002 beginning at some position interior to its periphery 1008. Though not shown separated from one another in FIG. 5, it is to be appreciated that the first and second constriction diffusion membranes 1200 and 1300 are operable to separate from one another, as discussed above, such that the reservoir is inflatable or dilatable.

As shown in FIG. 5, aqueous humor traveling through the fluid conduit 1500 along arrow 1602 exits the second end 1504 of the fluid conduit 1500 and diffuses or is otherwise injected into the reservoir 1010. As mentioned above, the reservoir 1010 may include the pore space of the first and second constriction diffusion membranes 1200 and 1300 and/or a region defined between the first and second constriction diffusion membranes 1200 and 1300. As shown in FIG. 5 the aqueous humor is shown exiting the fluid conduit 1500 into the reservoir 1010, which includes at least the region defined between the first and second constriction diffusion membranes 1200 and 1300.

As the evacuated aqueous humor percolates through the constriction and diffusion membranes of the aqueous humor diffusion member 1002, the aqueous humor generally percolates toward an exterior of the aqueous humor diffusion member 1002, as shown by arrows 1604A-1604E. It should be appreciated that arrows 1604A-1604E are not intended to represent actual paths of aqueous humor, but are instead intended to represent that aqueous humor is intended to percolate away from an interior region, such as the reservoir 1010, of the aqueous humor diffusion member 1002 or at least away from the second end 1504 of the fluid conduit 1500.

Figure 6:
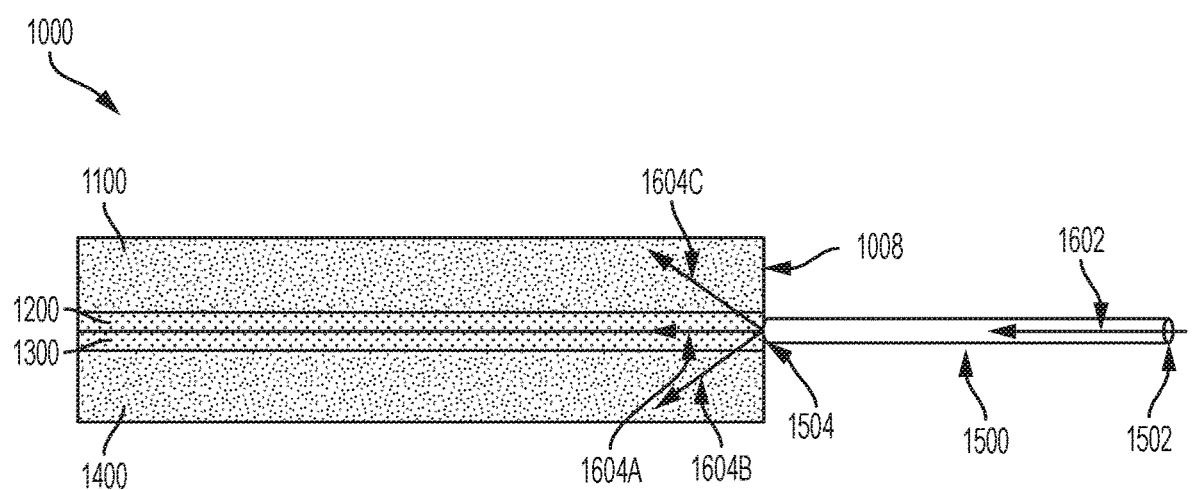
FIG. 6 is an illustration of a glaucoma drainage system consistent with various aspects of the present disclosure.

In some other embodiments, the second end 1504 of the fluid conduit 1500 is coupled to the periphery 1008 of the aqueous humor diffusion member 1002. For example, as shown in FIG. 6, the second end 1504 of the fluid conduit 1500 is coupled to the aqueous humor diffusion member 1002 at its periphery 1008. That is, in some embodiments, the second end 1504 is coupled to the aqueous humor diffusion member 1002 such that evacuated aqueous humor exiting the fluid conduit 1500 at the second end 1504 diffuses or is otherwise injected into the first and second constriction diffusion membranes 1200 and 1300 beginning at or proximate to a periphery 1008 of the aqueous humor diffusion member 1002.

In some such embodiments, as the evacuated aqueous humor percolates through the aqueous humor diffusion member 1002, the aqueous humor may percolate toward an interior of the aqueous humor diffusion member 1002 and/or may percolate toward an exterior of the aqueous humor diffusion member 1002. In some embodiments, as aqueous humor traveling through fluid conduit 1500 exits the second end 1504 of the fluid conduit 1500 between the first and second constriction diffusion membranes 1200 and 1300, as mentioned above. As similarly discussed above, the aqueous humor enters the reservoir 1010 of the aqueous humor diffusion member 1002, which may be defined between the first and second constriction diffusion membranes 1200 and 1300, or which may additionally or alternatively correspond with the pore space of the first and second constriction diffusion membranes 1200 and 1300. As mentioned above, the glaucoma drainage system 1000 is configured to allow the evacuated aqueous humor to percolate from the interior of the aqueous humor diffusion member 1002 toward an exterior of the aqueous humor diffusion member 1002.

Arrows 1604A-1604C of FIG. 6 are representative of aqueous humor generally percolating through the aqueous humor diffusion member 1002. As shown, arrow 1604A represents aqueous humor percolating through the aqueous humor diffusion member 1002 generally toward an interior region of the aqueous humor diffusion member 1002, while arrows 1604B and 1604C represent aqueous humor percolating through the aqueous humor diffusion member 1002 generally toward an exterior of the aqueous humor diffusion member 1002. As mentioned above, it should be appreciated that arrows 1604A-1604C are not intended to represent actual paths of aqueous humor, but are instead intended to represent that aqueous humor is intended to percolate at least away from the second end 1504 of the fluid conduit 1500. Moreover, though not shown separated from one another in FIG. 6, it will be appreciated that the first and second constriction diffusion membranes 1200 and 1300 are operable to separate from one another to define the reservoir 1010 therebetween.

In various embodiments, the second end 1504 of the fluid conduit 1500 may be coupled to the periphery 1008 of the aqueous humor diffusion member 1002 by way of an adhesive, a weld, stitching, or one or more mechanical fastening mechanisms. In some embodiments, the second end 1504 of the fluid conduit 1500 may be coupled to the periphery 1008 via one or more of the above-discussed thermal bonding methods to create an adhesive or cohesive bond between the material or the layers of material.

In various embodiments, the fluid conduit 1500 is coupled to the aqueous humor diffusion member 1002 such that evacuated aqueous humor exiting the fluid conduit 1500 at the second end 1504 diffuses into a constriction diffusion membrane prior to diffusing into a proliferation diffusion membrane. For example, as illustrated in FIGS. 5 and 6, the second end 1504 of the fluid conduit 1500 is coupled to the aqueous humor diffusion member 1002 such that evacuated aqueous humor exiting the fluid conduit 1500 at the second end 1504 diffuses into one or more of first and second constriction diffusion membranes 1200 and 1300 prior to diffusing into first and second proliferation diffusion membranes 1100 and 1400.

Unlike conventional designs, the glaucoma drainage system 1000 is soft and compliant, and does not require the preservation of a hollow aqueous humor reservoir internal to its aqueous humor diffusion member 1002. Conventional permeable hollow aqueous humor reservoirs must therefore be sufficiently rigid to preserve their volumes. Accordingly, in comparison to the glaucoma drainage system 1000, conventional designs are relatively rigid and susceptible to causing relative movement between the tissue and the device and thus tissue irritation which may lead to excessive scar formation and erosion of conventional devices.

As discussed above, in various embodiments, the aqueous humor diffusion member 1002 includes one or more adjacently situated diffusion membranes having adjacently facing interface surfaces that can slide or otherwise move relative to one another. In some embodiments, aqueous humor evacuated from the anterior chamber and introduced to the aqueous humor diffusion member 1002 operates as a lubricant that reduces friction between such interface surfaces and further facilitates sliding or relative movement between the uncoupled portions or regions. Specifically, as aqueous humor enters the aqueous humor diffusion member 1002, the aqueous humor percolates and diffuses across the various diffusion membranes. As the aqueous humor percolates and diffuses across the diffusion membranes, some aqueous humor diffuses across the boundaries separating adjacently situated diffusion membranes. In some embodiments, as the aqueous humor diffuses across the boundaries, it operates as a lubricant that reduces friction between the interface surfaces of the boundary which further adds to flexibility of the aqueous humor diffusion member 1002.

As discussed above, in some embodiments, the fluid conduit 1500 is soft and compliant and generally lacks a sufficient amount of structural integrity (e.g., hoop strength) to avoid collapsing under its own weight. In some embodiments, this lack of structural integrity results in a deformation of the fluid conduit 1500 to the extent that the lumen extending therethrough loses a significant portion of its cross-sectional area. In some embodiments, this lack of structural integrity results in a deformation of the fluid conduit 1500 to the extent that the aqueous humor in the anterior chamber is significantly restricted from even entering the lumen of the fluid conduit 1500. In some embodiments, to avoid these potential risks, the fluid conduit 1500 may be configured such one or more of its ends are sufficiently structurally sound in that they can be operable to maintain lumen integrity and avoid collapse or otherwise significant deformation of the lumen. In such embodiments, an intermediate portion of the fluid conduit 1500 situated between the first and/or second ends 1502 and 1504 is generally not structurally sound in that it cannot support its own weight. For example, the end (or an end portion) of the fluid conduit 1500 that is positioned within the anterior chamber is configured such that it is operable to maintain lumen integrity and avoid collapse or otherwise significant deformation of the lumen. In this example, the above discussed risks associated with relative movement and tissue irritation due to rigidity are generally avoided because the structurally sound end of the fluid conduit 1500 is suspended within the aqueous humor of the anterior chamber and thus does not interact with tissue in a manner that could lead to tissue irritation.

In various embodiments, the fluid conduit 1500 material may be subjected to one or more material conditioning processes to achieve structurally sound first and/or second ends. In some embodiments, one or more structural members, such as one or more stents or struts or reinforcing rings may be incorporated, integrated, or otherwise coupled to the first and/or second ends 1502 and 1504 to achieve the above-discussed structural integrity. These stents, struts, and/or reinforcing rings may be formed of any suitable biocompatible metallic or polymeric material discussed herein (e.g., FEP). In some embodiments, a localized densification to the first and/or second ends 1502 and 1504 of the fluid conduit 1500 can increase a structural integrity thereof to an extent sufficient to resist closure forces exerted on the ends by the body tissue.

Figure 7A:
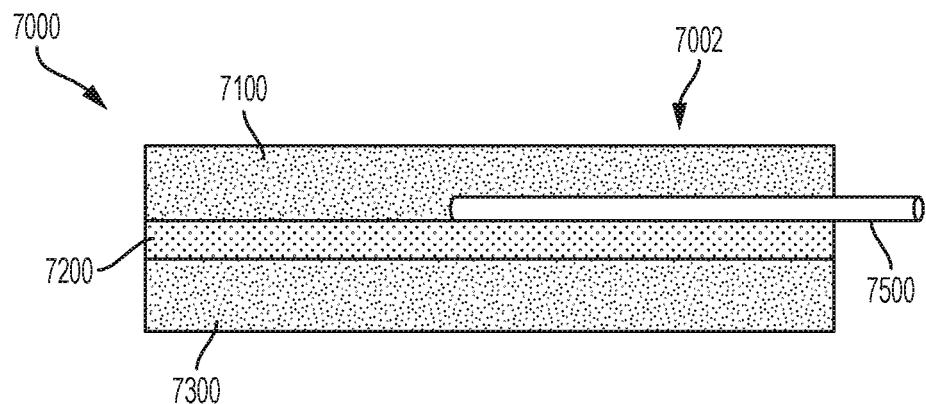
FIG. 7A is an illustration of a glaucoma drainage system in a deflated state consistent with various aspects of the present disclosure.
Figure 7B:
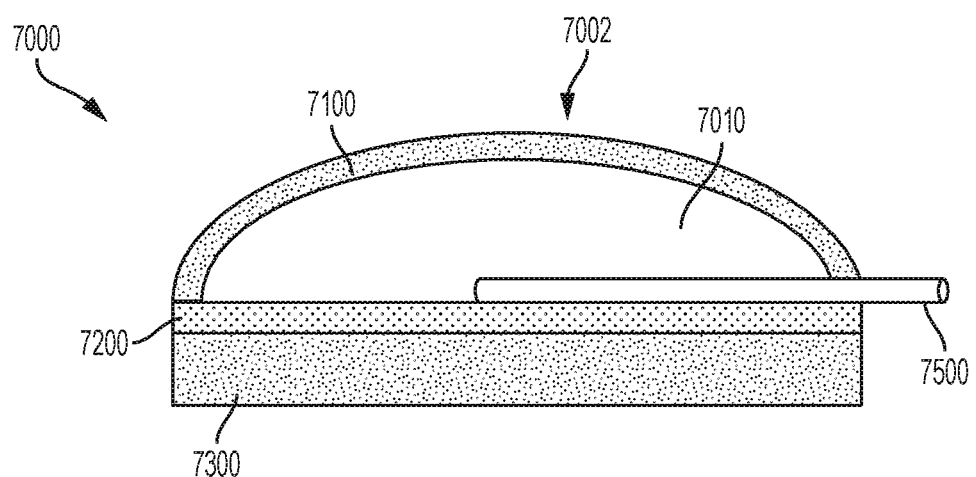
FIG. 7B is an illustration of a glaucoma drainage system in an inflated state consistent with various aspects of the present disclosure.

While the aqueous humor diffusion member 1002 illustrated and described herein includes a body defined by four diffusion membranes, the body of the aqueous humor diffusion member 1002 may alternatively be defined by as little as three diffusion membranes or in excess of four diffusion membranes without departing from the spirit or scope of the present disclosure. For example, while the above-discussed embodiments include an aqueous humor diffusion member 1002 including a plurality of constriction diffusion membranes and a plurality of proliferation diffusion membranes, in some embodiments, the aqueous humor diffusion member 1002 includes a constriction diffusion membrane that is sandwiched between a plurality of proliferation diffusion membranes. For example, turning now to FIGS. 7A and 7B, a glaucoma drainage system 7000 is shown and includes an aqueous humor diffusion member 7002 defined by a first proliferation diffusion membrane 7100, a first constriction diffusion membrane 7200 and a second proliferation diffusion membrane 7300. As shown, the first constriction diffusion membrane 7200 is situated between the first and second proliferation diffusion membranes 7100 and 7300. The first constriction diffusion membrane 7200 is configured to minimize, resist, or prevent tissue ingrowth and attachment, while the first and second proliferation diffusion membranes 7100 and 7300 are configured to permit tissue ingrowth and attachment. FIG. 7A shows the glaucoma drainage system 7000 in a deflated state. FIG. 7B shows the glaucoma drainage system 7000 in an inflated state, where aqueous humor is present within an inflatable or dilatable reservoir 7010 defined between the first proliferation diffusion membrane 7100 and the first constriction diffusion membrane 7200. While the glaucoma drainage system 7000 is shown in FIG. 7B in an inflated state where the glaucoma drainage system 7000 is not uniformly inflated (e.g., the first proliferation diffusion membrane 7100 is shown adopting a generally nonlinear configuration while the second proliferation diffusion membrane 7300 and the constriction diffusion membrane 7200 are shown in a generally linear configuration), it is to be appreciated that the glaucoma drainage system 7000 may deform uniformly (e.g., the second proliferation diffusion membrane 7300 and the constriction diffusion membrane 7200 may deform in a manner that mirrors the deformation of the first proliferation diffusion membrane 7100). The fluid conduit 7500 may be situated between the first constriction diffusion membrane 7200 and one of the first and second proliferation diffusion membranes 7100 and 7300. As shown, the fluid conduit 7500 is situated between the first constriction diffusion membrane 7200 and the first proliferation diffusion membrane 7100. The constriction and proliferation diffusion membranes may be coupled together along an entirety of their adjoining surface areas, or may include one or more unbonded or uncoupled areas or regions, consistent with the discussion above.

As shown in FIG. 7B the first constriction diffusion membrane 7200 and the first proliferation diffusion membrane 7100 are coupled along their peripheral edges, but include an unbonded or uncoupled region interior thereto, which defines the reservoir 7010. Thus, the unbonded or uncoupled regions between the first constriction diffusion membrane 7200 and the first proliferation diffusion membrane 7100 can separate from one another as the reservoir 7010 inflates or dilates as aqueous humor enters the reservoir 7010.

It is to be appreciated that the configuration of the glaucoma drainage system 7000 shown in FIGS. 7A and 7B includes a reservoir 7010 that is defined between a constriction diffusion membrane and a proliferation diffusion membrane. Such a configuration provides that tissue ingrowth is permitted along one side of the reservoir while tissue ingrowth is minimized, resisted, or prevented along another side of the reservoir. Moreover, as the constriction diffusion membrane and the proliferation diffusion membrane are associated with different permeabilities, the evacuated aqueous humor will percolate through the constriction diffusion membrane and the proliferation diffusion membrane at different rates.

In some embodiments, these differential rates at which aqueous humor diffuses into or percolates through different membranes can be utilized to influence, direct, or otherwise "steer" the aqueous humor through the aqueous humor diffusion member. In some embodiments, the aqueous humor diffusion member may be configured such that a higher percentage (or higher volume) of aqueous humor is directed toward a first exterior surface of the aqueous humor diffusion member than toward a second exterior surface of the aqueous humor diffusion member. Likewise, in some embodiments, the aqueous humor diffusion member may be configured such that a percentage of the aqueous humor is directed toward a periphery of the aqueous humor diffusion member. Such configurations provide that the evacuated aqueous humor can be steered toward a designated region of the surrounding tissue, such as a region of the surrounding tissue that is more adapted to absorb the evacuated aqueous humor and that is more adapted to facilitate absorption into the tear film.

For example, with continued reference to FIGS. 7A and 7B, in some embodiments, the first proliferation diffusion membrane 7100 a higher flux than the flux of the first constriction diffusion membrane 7200, and thus a higher percentage (or higher volume) of aqueous humor is steered toward an exterior surface extending along the first proliferation diffusion membrane 7100 relative to a percentage (or volume) of aqueous humor that is steered toward an exterior surface extending along the second proliferation diffusion membrane 7400. It is to be appreciated that, in some embodiments, such a configuration may be additionally or alternatively achieved by forming a first constriction diffusion membrane that has a higher flux than the flux of a second constriction diffusion membrane. In some embodiments, such a configuration is additionally or alternatively achieved by forming first proliferation diffusion membrane such that it has a higher flux than the flux of second proliferation diffusion membrane. In some embodiments, such a configuration may additionally or alternatively be achieved by forming the boundaries between adjacently situated diffusion membranes such that different boundaries are associated with different flux. Differing boundaries associated with different flux may be achieved through the manner in which adjacently situated diffusion membranes are adhered or bonded to one another.

While the glaucoma drainage system 7000 shown in FIGS. 7A and 7B includes a fluid conduit 7500 that is situated between the first proliferation diffusion membrane 7100 and the first constriction diffusion membrane 7200, and a reservoir 7010 that is defined between the first proliferation diffusion membrane 7100 and the first constriction diffusion membrane 7200, it should be appreciated that the first constriction diffusion membrane may be formed of a plurality of laminated layers of polymer material (as discussed above) and the fluid conduit 7500 may be situated between adjacent layers of the polymer material. Additionally or alternatively, in some examples, one or more of the adjacently facing layers of polymer material forming the constriction membrane may include one or more unbonded, uncoupled, or unlaminated areas or regions, consistent with the discussion above, such that the unbonded, uncoupled, or unlaminated areas or regions of the adjacently facing layers of polymer material remain free to separate from, or slide or move relative to one another and may define, at least in part, the reservoir 7010.

It should be appreciated that while the aqueous humor diffusion members illustrated and described herein are generally thin, flat, and circular (or ovular), the aqueous humor diffusion member may be of any suitable shape without departing from the spirit or scope of the disclosure. For instance, the aqueous humor diffusion member may be square, rectangular, trapezoidal, or some other polygonal shape, and may include chamfered or rounded edges between sides, and the sides may be linear or generally curved in nature. Alternatively, the aqueous humor diffusion member may have a generally continuous curved edge in that it is circular or ovular, or of another suitable shape (e.g., bean-shaped). Accordingly, the embodiments, and illustrations included herein should not be interpreted as limiting and those of skill in the art will appreciate that the aqueous humor diffusion member may be of any desired shape provided that the aqueous humor diffusion member is operable to accommodate a sufficient degree of evacuated aqueous humor and to help facilitate the reabsorption of aqueous humor to constitute an effective treatment for the patient.

Figure 8:
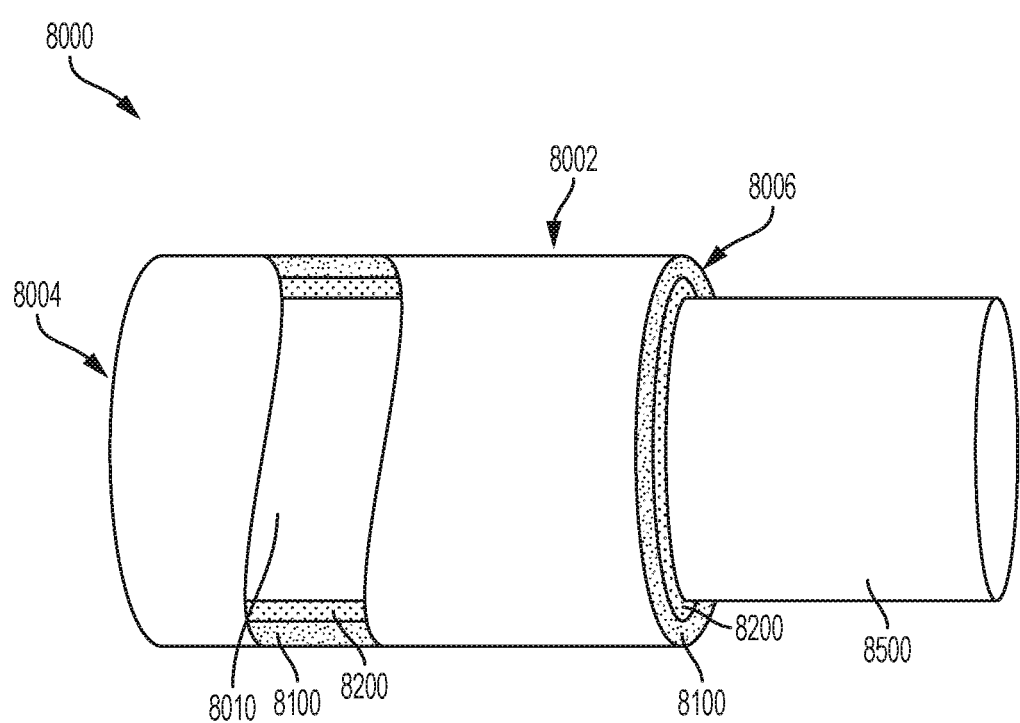
FIG. 8 is an illustration of a fluid conduit consistent with various aspects of the present disclosure.

In some alternative embodiments, an aqueous humor diffusion member may have a tubular or cylindrical profile including a plurality of concentrically situated diffusion membranes. For example, an aqueous humor diffusion member may include a tubular constriction diffusion membrane and a tubular proliferation diffusion membrane, where the tubular constriction diffusion membrane corresponds to an interior diffusion membrane that is concentric with the proliferation diffusion membrane, which defines an exterior of the aqueous humor diffusion member. Turing now to FIG. 8, a glaucoma drainage system 8000 is shown and includes an aqueous humor diffusion member 8002 that is defined by an outer tubular proliferation diffusion membrane 8100 that is concentric with an inner tubular constriction diffusion membrane 8200. A portion of the aqueous humor diffusion member 8002 is shown cut away to expose the interior region of the aqueous humor diffusion member 800. As shown, a reservoir 8010 is defined within a central lumen of the inner tubular constriction diffusion membrane 8200, and a fluid conduit 8500 is fluidly coupled with the reservoir 8010 at a second end 8006 of the aqueous humor diffusion member 8002. In some embodiments, the concentric diffusion membranes of the aqueous humor diffusion member 8002 shown in FIG. 8 may be uncoupled or partially uncoupled with one another, as discussed herein. In some embodiments, at least one end (e.g., the first end 8004 which is opposite the fluid conduit 8500) of the aqueous humor diffusion member 8002 is sealed to cause evacuated aqueous humor to percolate through the concentric diffusion membranes of the aqueous humor diffusion member 8002.

As discussed above, in various embodiments, the fluid conduit is a soft and compliant tubular member insertable into the anterior chamber of the eye. Generally, regardless of the specific surgical approach adopted by the physician, one or more of the fluid conduit and the aqueous humor diffusion member will be advanced or pushed during the implantation procedure. Soft, thin, and compliant tubular structures are generally difficult to advance through tissue. Accordingly, in various embodiments, the glaucoma drainage systems discussed herein may further include a stiffening member that is removably integrated with the glaucoma drainage systems. The removable stiffening member operates with the fluid conduit to temporarily form an installation assembly having column strength in excess of the column strength of the fluid conduit. For instance, in some embodiments, the stiffening member is disposed within the fluid conduit. In some other embodiments, the stiffening member is additionally or alternatively disposed about the fluid conduit. Treatment methods may include utilizing the stiffening member to advance one or more of the fluid conduit and the aqueous humor diffusion member into position, and then removing the stiffening member following the implantation.

Additionally or alternatively, in various embodiments, the fluid conduits of the various glaucoma drainage systems discussed here may be configured such that they include multiple lumens. In some embodiments, one or more of the lumens of the multilumen fluid conduit can be initially blocked, and wherein one or more of the lumens of the multilumen fluid conduit can be post-operatively unblocked to increase a fluid flow rate through the fluid conduit. Thus, in various embodiments, the various glaucoma drainage systems discussed herein may include one or more mechanisms that can be post-operatively modified to increase and/or decrease the aqueous humor transmission rate per unit of time of the glaucoma drainage system. Accordingly, the glaucoma drainage systems discussed herein are operable to dynamically change to accommodate a change in the anatomy or functioning of the patient's eye post-op without requiring the need for further invasive surgery.

In some embodiments, the glaucoma drainage systems discussed herein may be implanted ab-internally (e.g., from inside the eye), such as through a clear-corneal incision, and placed through the sclera and into a dissected subconjunctival space, as those of skill in the art will appreciate. In some other embodiments, the glaucoma drainage systems are implantable ab-externally (e.g., from outside of the eye), such as through a conjunctival incision, as those of skill in the art should appreciate. In some embodiments, a conjunctival radial incision is performed typically near the limbal junction, and blunt dissection of the conjunctiva is performed to expose the sclera and provide a site for placement of aqueous humor diffusion member. In some embodiments, this may require suturing of the aqueous humor diffusion member to the sclera. In some embodiments, a small needle, typically a 22 or 23 gauge needle, is also inserted near the scleral spur to provide a track for subsequent insertion and placement of the fluid conduit into the anterior chamber.

As discussed above, in various embodiments, the aqueous humor diffusion members discussed herein are formed of a plurality of diffusion membranes including a proliferation diffusion membrane and a constriction diffusion membrane, where the porosity or permeability to aqueous humor of the proliferation diffusion membrane exceeds the porosity of the constriction diffusion membrane. Thus, the disclosed aqueous humor diffusion members comprise a plurality of different membranes having different degrees of porosity (e.g., different quantity of pores and/or pores having different sizes). Generally, different diffusion membranes having different degrees of porosity will be associated with different rates at which aqueous humor diffuses into the associated membrane (also described as flux). For example, the aqueous humor diffusion member may be configured such that an amount of aqueous humor diffuses into the constriction diffusion membranes at a different rate (e.g., a lower flux) than the amount of aqueous humor diffuses into the proliferation diffusion membranes (e.g., higher flux). Thus, the aqueous humor diffusion member may be configured such that aqueous humor diffuses into a first region of the aqueous humor diffusion member at a different rate than the aqueous humor diffuses into a second region of the aqueous humor diffusion member.

As discussed above, in various embodiments, the layers of polymeric material(s) forming the diffusion membranes may be coupled together at one or more discrete locations to form stabilizing structures that extend through the diffusion membrane. In some embodiments, during a lamination process, the various layers forming the diffusion membrane may be laminated together such that one or more discrete pillar or column-like structures extend through the diffusion membrane from a first interface surface of the diffusion membrane to a second interface surface of the diffusion membrane. In various embodiments, these pillar or column-like structures can be formed of adhesives. In some embodiments, one or more of these pillars can effectively hold open or otherwise maintain an effective strainable, shearable, slideable interface such that the glaucoma drainage device is flexible and is operable to accommodate the evacuated aqueous humor. Additionally, in some embodiments, unintended expansion (e.g., ballooning) of the aqueous humor diffusion member beyond a designated amount or beyond a designated profile can be minimized and/or avoided by discretely bonding adjacently facing interface surfaces of adjacently situated diffusion membranes, as mentioned above.

As mentioned above, in various embodiments, the fluid conduit and/or the body of the aqueous humor diffusion member can be formed from soft and compliant materials to create a construct that conforms to the curvature of the eye, which helps minimizes relative movement between the glaucoma drainage systems and the surrounding tissue that can lead to tissue irritations, foreign body tissue response, excessive scar formation, and/or erosion. Another potential problem experienced with conventional designs includes erosion of the fluid conduit through the conjunctiva, generally proximate the region where the fluid conduit passes through the sclera and extends into the anterior chamber of the eye. Conjunctival erosion in this manner can lead to direct exposure of the anterior chamber, providing a pathway for bacteria to enter the eye, a risk of endophthalmitis, and potential loss of vision in the eye.

Though a number of approaches have been attempted to minimize the potential of such erosion through the conjunctiva, none of the known solutions include a singular device or system that combines aqueous humor drainage while protecting against erosion of the fluid conduit.

Turning now to FIGS. 9A to 11, in various embodiments, a glaucoma drainage system 9000 includes an aqueous humor diffusion member 9002 and a fluid conduit 9500. The fluid conduit 9500 may be consistent in construction, form, makeup, and function to the various fluid conduits (e.g., fluid conduit 1500) discussed above. Similarly, the aqueous humor diffusion member 9002 may be consistent in construction, form, makeup, and function to the various aqueous humor diffusion members (e.g., aqueous humor diffusion member 1002) discussed above, but with the exception that the aqueous humor diffusion member 9002 additionally includes one or more erosion elements 9600.

In various embodiments, an erosion element 9600 is an element, feature, component, or portion of the glaucoma drainage system 9000 that overlays a portion of the fluid conduit 9500 to help minimize erosion of the fluid conduit 9500 through one or more tissues of the eye when the glaucoma drainage system 9000 is implanted. As discussed above, in various embodiments, the glaucoma drainage system 9000 is implantable within a pocket formed between the conjunctiva and the sclera of the eye, as those of skill will appreciate.

In some instances, for example, the erosion element 9600 extends from the body of the glaucoma drainage system 9000 to overlay the fluid conduit 9500. The erosion element 9600 operates as a protective barrier between the fluid conduit 9500 and one or more surrounding tissues of the eye. For example, the glaucoma drainage system 9000 may be configured such that an erosion element 9600 extends along the fluid conduit 9500 between the fluid conduit 9500 and a conjunctiva of the eye when implanted. In some such embodiments, the erosion element 9600 helps minimize or even prevent erosion of the fluid conduit 9500 through the conjunctiva by forming a barrier between the fluid conduit 9500 and the conjunctiva when the glaucoma drainage device 9000 is implanted in the eye, as discussed further below.

In some embodiments, the erosion element 9600 forms an integral, non-separable element, feature, component, or portion of the glaucoma drainage system 9000. In some other embodiments, the erosion element 9600 is formed as a distinct element or component that is coupled with one or more portions of the glaucoma drainage system 9000. In some such embodiments, the erosion element 9600 may be coupled with the one or more portions of the glaucoma drainage system 9000 and thereby become integral to the glaucoma drainage system 9000. Alternatively, in some embodiments, the erosion element 9600 may be coupled with the one or more portions of the glaucoma drainage system 9000 such that the erosion element 9600 can be subsequently separated and removed from the glaucoma drainage system 9000.

As indicated above, the glaucoma drainage system 9000 may include multiple (or a plurality of) erosion elements 9600. In some such embodiments, the fluid conduit 9500 of the glaucoma drainage system 9000 may be isolated from interfacing with the surrounding tissue of the eye (e.g., a sclera or a conjunctiva) by the incorporation of multiple erosion elements 9600. That is, in some embodiments, the glaucoma drainage system 9000 may include one or more erosion elements 9600 that isolate the fluid conduit 9500 of the glaucoma drainage system 9000 from the tissue of the eye. For instance, the glaucoma drainage system 9000 may be configured such that erosion elements 9600 flank the fluid conduit 9500 on either side of a plane bisecting the fluid conduit 9500 along a longitudinal axis thereof. In such a configuration, for example, a first one of the erosion elements 9600 may extend along the fluid conduit 9500 between the fluid conduit 9500 and a sclera of the eye. Similarly, a second one of the erosion elements 9600 may extend along the fluid conduit 9500 between the fluid conduit 9500 and a conjunctiva of the eye. Such a configuration provides erosion protection for both a conjunctiva and a sclera of an eye when the glaucoma drainage device 9000 is implanted in the eye (e.g., when implanted within a pocket formed between the conjunctiva and the sclera), as the fluid conduit 9500 is prevented from directly interfacing with the conjunctiva and the sclera of the eye.

As mentioned above, with the exception of the erosion element 9600, the glaucoma drainage system 9000 is similar in construction, form, and makeup to the other glaucoma drainage systems discussed herein (e.g., glaucoma drainage system 1000). Thus, in various embodiments, the glaucoma drainage system 9000 comprises a multilayered construction and is configured to help drain aqueous humor from the anterior chamber of the eye by facilitating not only the evacuation of aqueous humor from within the anterior chamber of the eye, but also reabsorption of the evacuated aqueous humor by the body, for example. Like the glaucoma drainage system 1000, in various embodiments, the glaucoma drainage system 9000 similarly includes one or more constriction diffusion membranes and one or more proliferation diffusion membranes organized to optimize aqueous humor drainage and reabsorption (see discussion above).

In various embodiments, the erosion element 9600 includes a thin, flexible, porous membrane consistent in construction, form, and makeup with the various other thin, flexible, porous membranes discussed herein (e.g., the diffusion membranes discussed above). For example, the erosion element 9600 may include a microstructure that is configured to resist tissue ingrowth (e.g., a constriction diffusion membrane), or may alternatively include a microstructure that is configured to promote or permit tissue ingrowth (e.g., proliferation diffusion membrane). Alternatively, in some embodiments, the erosion element 9600 may comprise a multilayered construct including a first membrane configured to promote or permit tissue ingrowth (e.g., proliferation diffusion membrane) and a second membrane configured to resist tissue or cellular ingrowth (e.g., a constriction diffusion membrane). The permittive/resistive membranes in such embodiments are oriented to optimize their effect when the glaucoma drainage device 9000 is implanted in the eye. For instance, as discussed in greater detail below, in various embodiments, the erosion element 9600 is configured to promote or permit tissue ingrowth along an interface between the erosion element 9600 and a tissue of the eye (e.g., such as the sclera or the conjunctiva). It will thus be appreciated that the material of the erosion element 9600 may include any material and may be constructed according to any method discussed herein as being suitable for the diffusion membranes discussed above.

Accordingly, in various embodiments, the erosion element 9600 may be coupled with (or alternatively may be an extension of or integral with) any of the various proliferation diffusion membranes or constriction diffusion membranes discussed herein. Thus, in some embodiments, the erosion element 9600 may itself be a constriction diffusion membrane (e.g., configured to minimize, resist, or prevent tissue ingrowth) or a proliferation diffusion membrane (e.g., configured to permit tissue ingrowth). In some such embodiments, the erosion element 9600 is a constriction diffusion membrane coupled to or integral with a constriction diffusion membrane of the aqueous humor diffusion member. Additionally or alternatively, in some embodiments, the erosion element 9600 is a constriction diffusion membrane coupled to a proliferation diffusion membrane of the aqueous humor diffusion member. In some embodiments, the erosion element 9600 is a proliferation diffusion membrane coupled to a constriction diffusion membrane of the aqueous humor diffusion member. In some embodiments, the erosion element 9600 is a proliferation diffusion membrane coupled to or integral with a proliferation diffusion membrane of the aqueous humor diffusion member.

Figure 10:
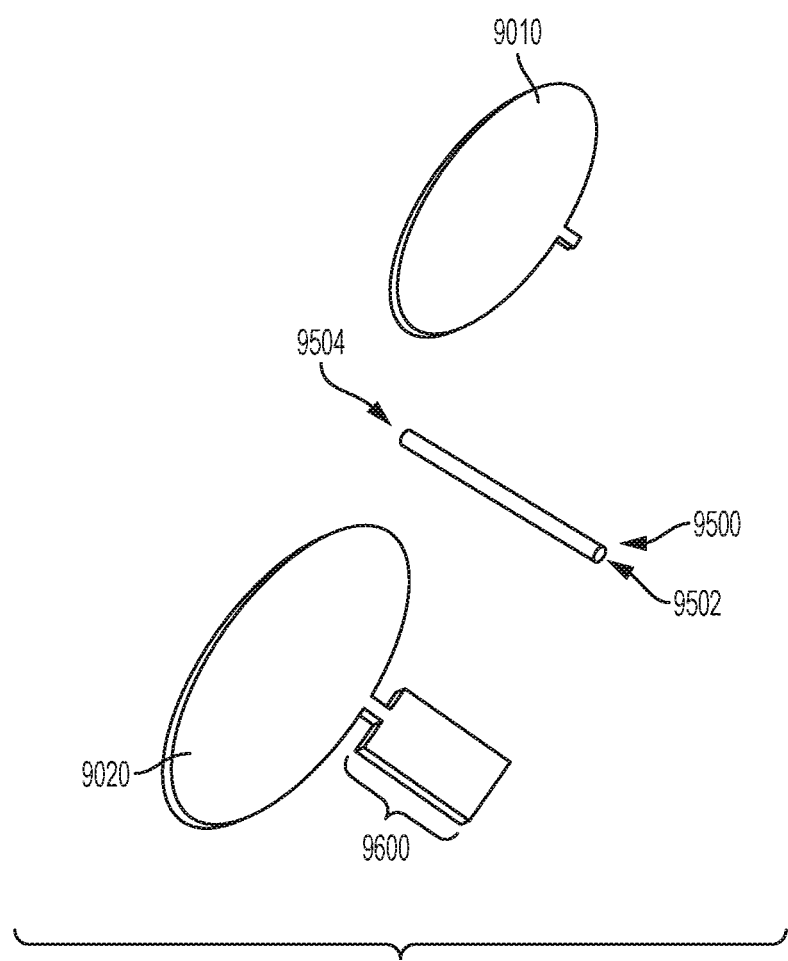
FIG. 10 is an exploded view of a glaucoma drainage system consistent with various aspects of the present disclosure.

Referring to FIGS. 9A to 9C and 10, a glaucoma drainage system 9000 is shown. FIG. 9A is a top view of the glaucoma drainage system. FIG. 9B is a cross-sectional view of the glaucoma drainage system 9000 taken along line 9B-9B in FIG. 9A. FIG. 9C is a cross-sectional view of the glaucoma drainage system 9000 taken along line 9C-9C in FIG. 9A. FIG. 10 is an exploded view of the glaucoma drainage system 9000.

As shown, the glaucoma drainage system 9000 includes an aqueous humor diffusion member 9002, a fluid conduit 9500 (e.g., a shunt), and an erosion element 9600. The aqueous humor diffusion member 9002 includes a plurality of layers including a first stratum 9010 and a second stratum 9020. The first and second stratum 9010 and 9020 each include one or more diffusion membranes configured to promote or permit tissue ingrowth (e.g., proliferation diffusion membrane) and/or one or more diffusion membranes configured to resist tissue ingrowth (e.g., a constriction diffusion membrane). Thus, it will be appreciated that the first stratum 9010 may be comprised of one or more diffusion membranes configured to promote or permit tissue ingrowth and one or more diffusion membranes configured to minimize, resist, or prevent tissue ingrowth. Similarly, it will be appreciated that the section stratum 9020 may additionally or alternatively be formed of one or more diffusion membranes configured to promote or permit tissue ingrowth and one or more diffusion membranes configured to minimize, resist, or prevent tissue ingrowth. Thus, it will be appreciated that the aqueous humor diffusion member 9002 may be similar in construction, form, and function to the various other aqueous humor diffusion members discussed herein.

As shown in FIGS. 9A-12, the glaucoma drainage system 9000 includes an erosion element 9600. The erosion element 9600 extends away from the aqueous humor diffusion member 9002 of the glaucoma drainage system 9000 as shown. In some embodiments, the erosion element 9600 extends away from the aqueous humor diffusion member 9002 along the fluid conduit 9500 between the fluid conduit 9500 and the aqueous humor diffusion member 9002. In some embodiments, the erosion element 9600 extends between the aqueous humor diffusion member 9002 and an end of the fluid conduit 9500 (e.g., a first end or a second end of the fluid conduit 9500) that is configured to access a biological fluid-filled body cavity, such as an anterior chamber of an eye, among other embodiments as will be appreciated by those of skill in the art.

Though illustrated in FIGS. 9A to 9C and 10 as including a rectangular shape, it will be appreciated that the erosion element 9600 may be of any suitable shape without departing from the spirit or scope of the disclosure. For instance, the erosion element 9600 may be square, rectangular, trapezoidal, or some other polygonal shape, and may include chamfered or rounded edges between sides, and the sides may be linear or generally curved in nature. The erosion element 9600 may have a generally continuous curved edge in that it is circular or ovular, or of another suitable shape (e.g., bean-shaped). It is to be appreciated that one of skill in the art will appreciate that the erosion element 9600 may be of any desired shape provided that the erosion element 9600 helps protect against erosion of the fluid conduit through tissue surrounding the fluid conduit and provided the erosion element 9600 can be placed within a subconjunctival space (such as a pocket formed between the conjunctiva and the sclera) as described herein.

In some embodiments, the erosion element 9600 extends along a length of the fluid conduit, but includes a length that is shorter than a length of the portion of the fluid conduit extending from the aqueous humor diffusion member 9002. In other embodiments, the erosion element 9600 extends along a length of the fluid conduit, and includes a length that is equal to or greater than a length of the portion of the fluid conduit extending from the aqueous humor diffusion member 9002. In some embodiments, the erosion element 9600 has a width that is greater than or equal to a diameter of the fluid conduit 9500. However, in some embodiments, the width of the erosion element 9600 may be less than the diameter of the fluid conduit, provided that the erosion element 9600 is not rendered ineffective against helping protect against erosion of the fluid conduit through surrounding tissue. Consistent with the versatility in suitable sizes and shapes of the erosion element 9600 discussed above, it will be appreciated that the width of the erosion element 9600 may remain constant along the length of the erosion element 9600, or alternatively, the width of the erosion element 9600 may vary along the length of the erosion element 9600. For example, the width may taper (linearly or nonlinearly) along the longitudinal length of the erosion element.

In some embodiments, the erosion element 9600 may be configured such that it is more abrasion resistant in high wear or high abrasion areas (e.g., areas where the fluid conduit 9500 has a potential to move relative to the erosion plate 9600). Resistance to abrasion in such areas may be accomplished according to any known methods, including material compositions and/or material thickness. A thickness of the erosion element 9600 may thus vary along the length of the erosion element 9600, and/or may vary laterally across its width. For example, the thickness may taper (linearly or nonlinearly) along the length of the erosion element 9600 and/or transversely thereacross. For instance, a thickness of the erosion element 9600 along a longitudinally extending centerline may be in excess of a thickness of the erosion element 9600 along one or more of its longitudinally extending edges. Alternatively, it will be appreciated that a thickness of the erosion element 9600 along a longitudinally extending centerline may be less than a thickness of the erosion element 9600 along one or more of its longitudinally extending edges. Additionally or alternatively, a thickness of the erosion element 9600 along a section of its longitudinal length may be in excess of a thickness of the erosion element 9600 along a second section of its longitudinal length. For example, if a region where the fluid conduit 9500 accesses the fluid-filled body cavity corresponds to a high abrasion region, a section of the erosion element 9600 that is more proximate the end of the fluid conduit 9500 that is configured to access the fluid-filled body cavity may be thicker than is a section of the erosion element 9600 that is more proximate the aqueous humor diffusion member 9002. It is to be appreciated that a thickness of the erosion plate 9600 can be optimized in high wear or high abrasion areas to reduce a risk of premature failure of the glaucoma drainage system 9000, due to abrasion of the erosion plate 9600 by the fluid conduit 9500. These variances in thickness may be achieved through selective layering of materials that collectively form the erosion element 9600 or other known methods.

In some embodiments, the erosion element 9600 may be longitudinally spaced apart from the aqueous humor diffusion member 9002, or may include a region of reduced width (e.g., as illustrated in FIG. 10) and/or thickness (not illustrated) extending between the erosion element 9600 and the aqueous humor diffusion member 9002 along those regions of the fluid conduit 9500 that are associated with a low risk of erosion through the surrounding tissue. For example, if the portion of the fluid conduit 9500 adjacent the aqueous humor diffusion member 9002 is associated with a low risk of erosion through the surrounding tissue, a region of reduced width and/or thickness of the erosion element 9600 may be situated adjacent this region of the fluid conduit 9500. Alternatively, the erosion element 9600 may be configured such that the fluid conduit 9500 is exposed to the surrounding tissue in this region of low risk for erosion. Thus, in some examples, the erosion element 9600 may not extend from the aqueous humor diffusion member 9002.

In some embodiments, the erosion element 9600 is coupled to the fluid conduit 9500. The erosion element 9600 may be coupled to the fluid conduit 9500 continuously along a length of the fluid conduit 9500, or alternatively along the fluid conduit 9500 at one or more discrete locations. The erosion element 9600 may be coupled to the fluid conduit 9500 according to any known methods including, but not limited to suturing or stitching of the erosion element along the length of the conduit. In some embodiments, suturing can be a series of interrupted sutures or a continuous running stitch. Additionally or alternatively, the fluid conduit 9500 can be mechanically adhered to the erosion element 9600 by partially melting the fluid conduit 9500 into the microporous structure of the erosion element 9600. In some embodiments, the erosion element 9600 may be coated with an adhesive that is tacky such that the fluid conduit 9500 can releasably stick to the erosion element 9600. In some embodiments, one or more bands of material (e.g., microporous material) can have their ends adhered to the erosion element 9600 such that an eyelet is formed between the band of material and the erosion element 9600 and the fluid conduit 9500 can be threaded through the gap.

Figure 11:
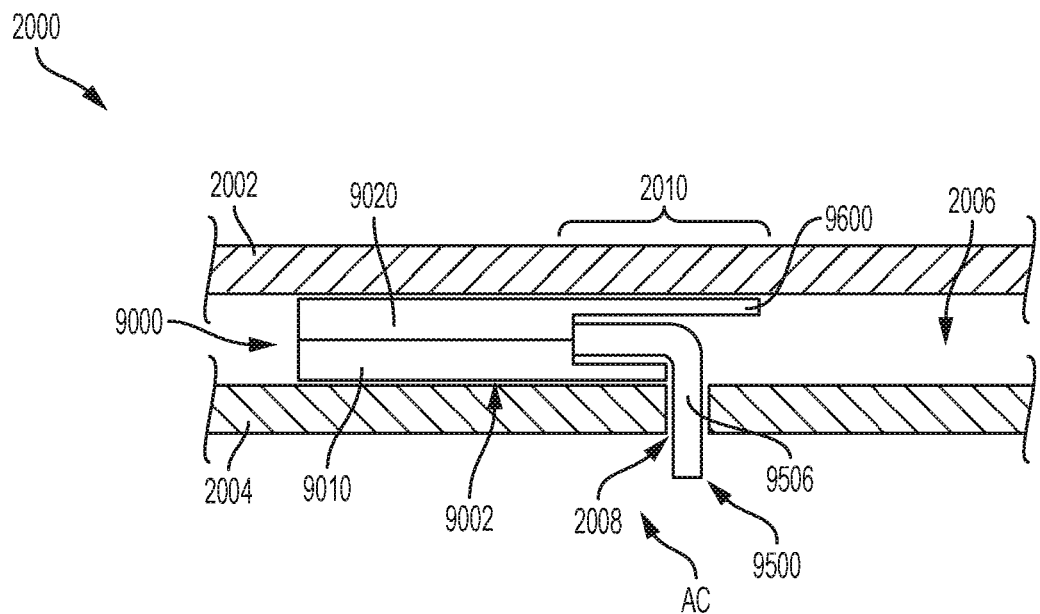
FIG. 11 is an illustration of a glaucoma drainage system implanted within an eye tissue consistent with various aspects of the present disclosure.
Figure 12:
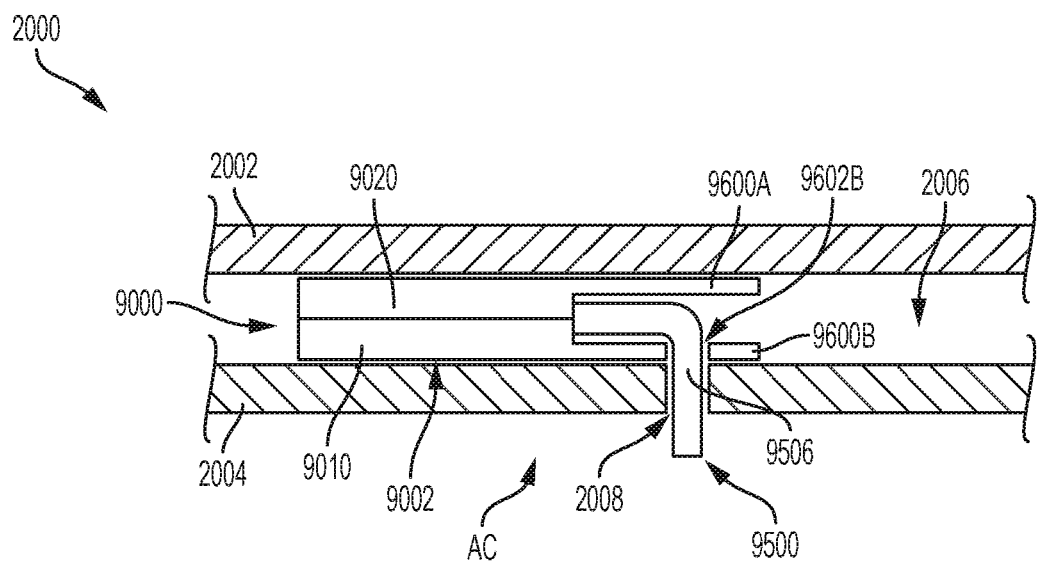
FIG. 12 is an illustration of a glaucoma drainage system implanted within an eye tissue consistent with various aspects of the present disclosure.

As discussed above, when used to treat conditions such as glaucoma, the glaucoma drainage system 9000 may be situated within a subconjunctival space (e.g., a pocket formed between the conjunctiva and the sclera of the eye). The glaucoma drainage system 9000 is situated such that it adopts a relatively flat and minimal radial profile within the subconjunctival space, and such that the anterior chamber of the eye can be accessed by the fluid conduit 9500. With reference now to FIGS. 11 and 12, glaucoma drainage systems are illustrated in implanted configurations. FIG. 11 includes a glaucoma drainage system 9000 having an aqueous humor diffusion member 9002, a fluid conduit 9500, and an erosion element 9600. FIG. 12 includes a glaucoma drainage system 9000 having an aqueous humor diffusion member 9002, a fluid conduit 9500, and a plurality of first and second erosion elements 9600A and 9600B.

With reference to FIG. 11, for example, the glaucoma drainage system 9000 is shown disposed in a subconjunctival space 2006 between the conjunctiva 2002 and the sclera 2004 of the eye 2000. The glaucoma drainage system 9000 is shown oriented such that the first stratum 9010 extends along the sclera 2004 and such that the second stratum 9020 extends along the conjunctiva 2002. It will be appreciated that the portion of the second stratum 9020 that interfaces with the conjunctiva 2002 may be configured to promote or permit tissue ingrowth, as discussed above. It will also be appreciated that the portion of the first stratum 9010 that interfaces with the sclera may additionally or alternatively be configured to promote or permit tissue ingrowth, as discussed above. Such configurations help minimize relative movement between the aqueous humor diffusion member 9002 and the surrounding tissue.

Moreover, the fluid conduit 9500 is shown in FIG. 11 as extending from the aqueous humor diffusion member 9002, and extending through a scleral access, perforation, or hole 2008 (e.g., made by a physician during the implantation procedure according to known methods) such that a first end 9502 accesses the anterior chamber (AC). Additionally, as shown the erosion element 9600 extends between the fluid conduit 9500 and the conjunctiva 2002 of the eye 2000. In particular, the erosion element 9600 extends between the fluid conduit 9500 and the conjunctiva 2002 such that a portion of the erosion element 9600 is positioned adjacent or proximate the scleral access 2008 and/or adjacent or proximate the portion 9506 of the fluid conduit extending through the scleral access 2008. Such a configuration provides that the conjunctiva 2002 is not directly exposed to the fluid conduit 9500. Instead, as shown, the erosion element 9600 extends along the conjunctiva 2002. This configuration helps protect against erosion of the fluid conduit 9500 thorough the conjunctiva 2002, as the erosion element 9600 operates as a protective barrier between the conjunctiva 2002 and the fluid conduit 9500. For example, the erosion element 9600 operates as a protective barrier between the fluid conduit and a portion 2010 of the conjunctiva positioned adjacent or proximate the scleral access 2008, as shown.

It will be appreciated that, the portion of the erosion element 9600 that interfaces with the conjunctiva 2002 may be configured to promote or permit tissue ingrowth, as discussed above. Such a configuration helps minimize relative movement between the erosion element 9600 and the conjunctiva, even where relative movement may exist between the fluid conduit 9500 and the erosion element 9600.

Though the erosion element 9600 is shown in FIG. 11 as including a portion that extends beyond the scleral access 2008 (and thus the portion of the fluid conduit 9500 extending through the scleral access), in some embodiments, the erosion element 9600 may extend up to or even short of the scleral access 2008 provided the erosion element 9600 is not rendered ineffective against helping protect against erosion.

In some embodiments, when implanted, aqueous humor enters the first end 9502 of the fluid conduit 9500 and travels to a second end 9504 of the fluid conduit in fluid communication with the aqueous humor diffusion member 9002. In some embodiments the second end 9504 is positioned within the aqueous humor diffusion member 9002 in the same manner discussed above with regard to the second end 1504 of the fluid conduit 1500 and the aqueous humor diffusion member 1002. Accordingly as discussed above, the evacuated aqueous humor enters a reservoir defined within the aqueous humor diffusion member 9002 and percolates through the various diffusion membranes of the aqueous humor diffusion member 9002, where the aqueous humor is then absorbable by the surrounding and/or ingrown tissue.

Turning now to FIG. 12, a glaucoma drainage system 9000 is shown disposed in a subconjunctival space 2006 between the conjunctiva 2002 and the sclera 2004 of the eye 2000. The configuration of the glaucoma drainage system 9000 shown in FIG. 12 is similar to the configuration of the glaucoma drainage system 9000 shown in FIG. 11 with the exception that the glaucoma drainage system 9000 shown in FIG. 12 includes two erosion elements (e.g., a first erosion element 9600A and a second erosion element 9600B). The first erosion element 9600A, corresponds in construction, form, and function to the erosion element 9600 discussed above with regard to FIG. 11. It will be appreciated that while the glaucoma drainage system 9000 shown in FIG. 12 includes second erosion element 9600B in combination with first erosion element 9600A, a glaucoma drainage system may include second erosion element 9600B without also requiring first erosion element 9600A. That is, in some embodiments, the glaucoma drainage system 9000 may be configured to include an erosion element that extends between the fluid conduit 9500 and the sclera 2004 without also requiring an erosion element that extends between the fluid conduit 9500 and the conjunctiva 2002.

Additionally, as shown in FIG. 12, the fluid conduit 9500 extends through an aperture 9602B of the second erosion element 9600B before extending through the scleral access, perforation, or hole 2008 (e.g., made by a physician during the implantation procedure according to known methods) and into the anterior chamber (AC). Thus, it will be appreciated that in various embodiments, an erosion element (such as second erosion element 9600B) may include one or more incisions, perforations, or apertures that are configured to accommodate the fluid conduit 9500. In some embodiments, the second erosion element 9600B is constructed or manufactured with such a preformed aperture. In some other embodiments, an incision, perforation, or aperture may be formed in the erosion element during the implantation procedure or just prior thereto. In some embodiments, the incision, perforation, or aperture is formed by the physician or a physician's assistant.

As shown, the second erosion element 9600B extends between the fluid conduit 9500 and the sclera 2004, while the first erosion element 9600A extends between the fluid conduit 9500 and the conjunctiva 2002. Though the second erosion element 9600B shown in FIG. 12 includes aperture 9602B and thus a portion thereof that extends beyond the scleral access 2008, it will be appreciated that the second erosion element 9600B may not extend up to or beyond the scleral access 2008, and thus may not require an aperture 9602B. In such configurations, the second erosion element 9600B may extend between the sclera 2004 and the fluid conduit 9500 to a position short of the scleral access 2008 (not shown).

Configurations including an erosion element that is positionable between the fluid conduit 9500 and the sclera 2004 provide that the sclera 2004 is not directly exposed to the fluid conduit 9500. Such configurations help protect against erosion of the fluid conduit 9500 thorough the sclera 2004, as such erosion elements operate as a protective barrier between the sclera 2004 and the fluid conduit 9500.

In some embodiments, the portion of the second erosion element 9600B that interfaces with the sclera 2004 may be configured to promote or permit tissue ingrowth, as discussed above. Such a configuration helps minimize relative movement between the second erosion element 9600B and the sclera 2004, even where relative movement may exist between the fluid conduit 9500 and the second erosion element 9600B.

In various embodiments, one or more portions of the glaucoma drainage systems discussed herein may include or be coated by one or more therapeutic agents, such as one or more glaucoma medications, as those of skill will appreciate. Additionally or alternatively, in various embodiments, one or more portions of the glaucoma drainage systems discussed herein may include one or more markers for visually or electronically (e.g., radiopaque markers) determining proper placement of the glaucoma drainage system within the anatomy.

It should be appreciated that in various embodiments, the diffusion membrane materials may additionally or alternatively be subjected to one or more processes to remove air trapped within the various voids within the material (e.g., denucleation). These processes may be combined with one or more of the hydrophilic coating processes discussed above. Entrapped air can sometimes interfere with wetting or saturation of the material with aqueous humor which could impair the efficiency of the aqueous humor diffusing into the aqueous humor diffusion member and being reabsorbed by the body. In some embodiments, entrapped air can be removed by soaking the material in a series of baths. In some embodiments, these baths may progress from one or more alcohol baths to one or more sterile water baths.

Example 1

A medical device was constructed according to the following method. A bottom sacrificial compression layer of thick distended PTFE tape was prepared by laser cutting a small coupon of PTFE distended tape. In particular, the shape of the glaucoma drainage device laser cut from the sacrificial PTFE layer corresponded to the shape of the first stratum 9010 illustrated in FIG. 10. All chads were removed and the sacrificial layer was aligned and placed on a jig plate configured to accommodate the small coupon. A first coupon of microporous diffusion material (e.g., multilayered ePTFE) was then placed over the small coupon of sacrificial PTFE material. The shape of the glaucoma drainage device was not laser cut into the first coupon of microporous diffusion material. The first coupon of microporous diffusion material was oriented such that the tissue ingrowth proliferation side of the first coupon of microporous diffusion material was facing downwardly toward the sacrificial PTFE coupon.

A layer of adhesive film (e.g., FEP) was then prepared by laser cutting the shape of the glaucoma drainage device into the adhesive film identical in size and location to that done in the sacrificial PTFE coupon. All chads were then removed, and the adhesive film layer was aligned and placed over the microporous diffusion, ensuring that the adhesive film lies flat with no wrinkles or foldovers. A second coupon of microporous diffusion material (e.g., multilayered ePTFE) was then placed over the adhesive film. The shape of the glaucoma drainage device was not laser cut into the second coupon of microporous diffusion material. The second coupon of microporous diffusion material was oriented such that the tissue ingrowth proliferation side of the second coupon of microporous diffusion material was facing upwardly away from the adhesive film. A top sacrificial compression layer of thick distended PTFE tape was then placed over the second coupon of microporous diffusion material. The shape of the glaucoma drainage device was not laser cut into the top sacrificial compression layer of thick distended PTFE tape. With this lamination stack setup, the jig was compressed such that the first and second coupons of microporous diffusion material were uniformly compressed with the exception of laser cut areas corresponding to the size and shape of the glaucoma drainage device. That is, with the cut out of the glaucoma drainage device shape performed in the first bottom sacrificial later layer, only minimal force insufficient to create a bond between the first and second coupons of microporous diffusion material is applied to the area corresponding in size and shape to the glaucoma drainage device. Similarly, because a chad corresponding to the size and shape of the glaucoma drainage device was removed from the adhesive layer during the layup process, no adhesive film is applied to the corresponding areas of the first and second coupons of microporous diffusion material.

The jig and layup was then placed onto a heated press platen, such as that of a desktop hot press, preheated to about 280 C, and sufficiently compressed for designated period of at least 5 minutes for a bond to occur between the first and second coupons of microporous diffusion material and adhesive film, while avoiding any significant bonding of the laminate to the sacrificial layers. The laminate was then removed from the press and allowed to cool to room temperature.

The resulting laminate was then laser cut to final size. In particular, the cut line followed the trace of the glaucoma drainage device shape formed in the sacrificial first layer of PTFE, offset a short distance (~1 mm) outward so that the perimeter of the device shape included the portion of first and second coupons of microporous diffusion material that were bonded together.

A fluid conduit formed of a silicone tube was inserted between the uncompressed layers leading into the interior of glaucoma drainage device by separating uncompressed layers slightly and inserting the tube up to an interior perimeter defined by where the first and second coupons of microporous diffusion material were bonded together. To tube was then secured to the glaucoma drainage device according to known methods.

Example 2

A medical device was constructed according to the following method. A bottom sacrificial compression layer of thick distended PTFE tape was prepared by laser cutting a small coupon of PTFE distended tape. The shape of a glaucoma drainage device consistent with the above was laser cut from the small coupon, and included approximately an 8 mm circular dimension. In particular, the shape of the glaucoma drainage device laser cut from the small coupon corresponded to the shape of the second stratum 9020 illustrated in FIG. 10. That is, the shape of the glaucoma drainage device laser cut from the small coupon included an ovular aqueous humor diffusion region and a rectangular erosion element consistent with the disclosure above. All chads were removed and the sacrificial layer was aligned and placed on a jig plate configured to accommodate the small coupon. A first coupon of microporous diffusion material (e.g., multilayered ePTFE) was then placed over the small coupon of sacrificial PTFE material. The shape of the glaucoma drainage device was not laser cut into the first coupon of microporous diffusion material. The first coupon of microporous diffusion material was oriented such that the tissue ingrowth proliferation side of the first coupon of microporous diffusion material was facing downwardly toward the sacrificial PTFE coupon.

A layer of adhesive file (e.g., FEP) was then prepared by laser cutting the shape of the glaucoma drainage device, less the rectangular erosion element feature, into the adhesive film identical in size and location (but with the exception of the rectangular erosion element feature) to that done in the sacrificial PTFE coupon. In particular, the shape of the glaucoma drainage device laser cut from the adhesive film corresponded to the shape of the first stratum 9010 illustrated in FIG. 10. All chads were then removed, and the adhesive film layer was aligned and placed over the microporous diffusion, ensuring that the adhesive film lies flat with no wrinkles or foldovers. A second coupon of microporous diffusion material (e.g., multilayered ePTFE) was then placed over the adhesive film. The shape of the rectangular erosion element was laser cut into the second coupon of microporous diffusion material, identical in size and location to that done in the sacrificial PTFE coupon. All chads were then removed, and the second coupon of microporous diffusion material was oriented such that the tissue ingrowth proliferation side of the second coupon of microporous diffusion material was facing upwardly away from the adhesive film.

A top sacrificial compression layer of thick distended PTFE tape was then placed over the second coupon of microporous diffusion material. The shape of the glaucoma drainage device was not laser cut into the top sacrificial compression layer of thick distended PTFE tape. With this lamination stack setup, the jig was compressed such that the first and second coupons of microporous diffusion material were uniformly compressed with the exception of laser cut areas corresponding to the size and shape of the glaucoma drainage device cut into the first sacrificial layer.

The jig and layup was then placed onto a heated press platen, such as that of a desktop hot press, preheated to about 280 C, and sufficiently compressed for designated period of at least 5 minutes for a bond to occur between the first and second coupons of microporous diffusion material and adhesive film, while avoiding any significant bonding of the laminate to the sacrificial layers. The laminate was then removed from the press and allowed to cool to room temperature.

The resulting laminate was then laser cut to final size consistent with the laser cutting process of Example 1, with the exception that no offset was cut around the rectangular portion defining the erosion element. The resulting laminate included a bottom microporous diffusion material layer consistent in size and shape with the shape of the second stratum 9020 illustrated in FIG. 10, and a top microporous diffusion material layer consistent in size and shape with the shape of the first stratum 9010 illustrated in FIG. 10.

A fluid conduit formed of a silicone tube was inserted between the uncompressed layers leading into the interior of glaucoma drainage device by separating uncompressed layers slightly and inserting the tube up to an interior perimeter defined by where the first and second coupons of microporous diffusion material were bonded together. To tube was then secured to the glaucoma drainage device according to known methods.

Example 3

The hydrophobic ePTFE device assembly from Example 1 or 2 was hydrophilically coated in the following manner. The ePTFE was wet out by directly delivering about 1 ml of 100% isopropyl alcohol through device's fluid conduit (e.g., silicone tubing) and flushed through the ePTFE reservoir. The excess alcohol was then flushed out of device with about 1 ml deionized water (nominal resistance ~$10^6$ ohm) directed through the fluid conduit and ePTFE reservoir. Approximately 1 ml of 0.2 wt % polyvinylalcohol aqueous solution was then directly flushed through the fluid conduit and ePTFE reservoir, and allowed to equilibrate for approximately 10 minutes. Approximately 1 ml of distilled water was them flushed through the fluid conduit and ePTFE reservoir. Approximately 1 ml of crosslinking aqueous solution (2 vol % glutaraldehyde in approximately 0.3 Molar hydrochloric acid was raised in temperature to about 40 C and directly flushed through the device, and allowed to equilibrate for approximately 15 minutes. Approximately 2.5 ml of deionized water was flushed directly through the fluid conduit and ePTFE reservoir. The material was then equilibrated in a beaker of approximately 40 ml of fresh deionized water.

The resulting assembly was then dried in an air oven at 115 C for approximately 10 minutes.

Example 4

A device from Example 3 was implanted in the superotemporal quadrant in the subconjunctival plane of a New Zealand White Rabbit and evaluated for an in-life period of 14 days. During implantation, a tunnel was made at the limbus using a 25 gauge needle, in which the fluid conduit was passed into the anterior chamber. To visualize the reservoir of aqueous fluid, an aqueous solution of 0.01% sodium fluorescein was used. Infused fluorescein is excited by ultraviolet light and strongly fluoresces, easily visible in a darkened environment. Prior to sacrifice, a 0.01% sodium fluorescein aqueous solution was injected into the anterior chamber of the implanted eye through a 30 gauge needle at a nominal flowrate of approximately 10 µl/min for a period of about 10 minutes. At the 14 day timepoint, a strongly fluorescent reservoir was observed as well as fluorescent vessels emanating from the implant reservoir area.

The inventive scope of this application has been described above both generically and with regard to specific examples. It will be apparent to those skilled in the art that various modifications and variations can be made in the examples without departing from the scope of the disclosure. Likewise, the various components discussed in the examples discussed herein are combinable. Thus, it is intended that the examples cover the modifications and variations of the inventive scope.

What is claimed is:

1. A biological fluid drainage device for draining a fluid from a fluid-filled body cavity, the device comprising:
   a body formed from one or more microporous diffusion materials having opposing sides and including a plurality of microporous membranes formed therein, the one or more microporous diffusion materials including a first microporous diffusion material and a second microporous diffusion material, the first microporous diffusion material comprising a first microporous membrane that is situated to a second microporous membrane so as to form a first proliferation diffusion side at the first microporous membrane and a first constriction diffusion side at the second microporous membrane, the second microporous diffusion material comprising a third microporous membrane that is situated to a fourth microporous membrane so as to form a second proliferation diffusion side at the fourth microporous membrane and a second constriction diffusion side at the third microporous membrane, the second and third microporous membranes being situated between the first and fourth microporous membranes such that the first and second proliferation diffusion sides are facing outwardly from each other and the first and second constriction diffusion sides are facing inwardly toward each other, and the second and third microporous membranes being sealed together along peripheral edges of the first and second microporous diffusion materials to define an inflatable reservoir disposed between the second and third microporous membranes, the reservoir being configured to accumulate the fluid, the first and second microporous diffusion materials being sealed so as to allow drainage of the fluid to an environment exterior to the device, including at or near a periphery of the reservoir; and
   a fluid conduit having a first end and a second end, the first end being fluidly coupled to the reservoir and the second end extending outside the body and being insertable into the fluid-filled body cavity such that the fluid from the fluid-filled body cavity is transferrable to the reservoir.

2. The device of claim 1, wherein first portions of the second and third microporous membranes are partially bonded with each other within the inflatable reservoir and adjacent second portions of the second and third microporous membranes are separate from one another.

3. The device of claim 1, wherein the second and third microporous membranes each have a permeability that is different from a permeability of each of the first and fourth microporous membranes.

4. The device of claim 1, wherein at least one of the first, second, third, and fourth microporous membranes comprise expanded polytetrafluoroethylene.

5. The device of claim 1, further comprising a fifth microporous membrane situated adjacent the body, wherein the fifth microporous membrane extends between the body and the second end of the fluid conduit.

6. The device of claim 5, wherein the fifth microporous membrane is configured to permit tissue ingrowth.

7. The device of claim 5, wherein the fifth microporous membrane is coupled to the fluid conduit.

8. The device of claim 5, wherein the fifth microporous membrane is integral with one of the first, second, third or fourth microporous membranes.

9. The device of claim 8, wherein the fifth microporous membrane and the first microporous membrane are the same microporous membrane.

10. The device of claim 5, further comprising a sixth microporous membrane situated adjacent the body, wherein the sixth microporous membrane extends between the body and the second end of the fluid conduit.

11. The device of claim 10, wherein the sixth microporous membrane and the fourth microporous membrane are the same microporous membrane.

12. The device of claim 11, wherein the sixth microporous membrane includes a perforation sized to accommodate the fluid conduit such that the fluid conduit can be extended through the perforation and into the fluid-filled body cavity when implanted.

13. The device of claim 1, wherein the first and fourth microporous membranes are each configured to remain permeable to the fluid after ingrowth of tissue occurs in the first and fourth microporous membranes.

14. The device of claim 1, wherein the reservoir is configured to inflate when the fluid is transferred into the reservoir.

15. The device of claim 14, wherein the body is configured to adopt a predetermined profile as a result of inflation of the reservoir.

16. The device of claim 1, wherein the first, second, third, and fourth microporous membranes each comprise a plurality of small holes, and wherein the plurality of small holes of the second and third microporous membranes are sized to resist tissue ingrowth, and wherein the plurality of small holes of the first and fourth microporous membranes are sized to permit tissue ingrowth.

17. The device of claim 1, wherein the fluid-filled body cavity is an anterior chamber of an eye and wherein the fluid is aqueous humor.

18. The device of claim 1, wherein the first and second microporous diffusion materials each are uncompressed, including adjacent to the mating peripheral edges of the first and second microporous diffusion materials.

19. A biological fluid drainage device for draining a fluid from a fluid-filled body cavity, the device comprising:
- a body including a microporous diffusion material having a plurality of membranes formed therein such that there is a proliferation diffusion side and a constriction diffusion side that is opposite the proliferation diffusion side, the body having an internal reservoir formed therein such that the internal reservoir is surrounded by the constriction diffusion side of the microporous diffusion material and such that the proliferation diffusion side faces outwardly away from the internal reservoir with a periphery of the proliferation diffusion side exposed to an environment exterior to the device so as to allow drainage of biological fluid at or near the periphery; and
- a fluid conduit having a first end and a second end, the first end being fluidly coupled to the internal reservoir and the second end extending outside the body and being insertable into the fluid-filled body cavity such that the fluid from the fluid-filled body cavity is transferrable to the reservoir.

20. A biological fluid drainage device for draining a fluid from a fluid-filled body cavity, the device comprising:
- a body including a first porous membrane coupled to a second porous membrane to define an internal reservoir disposed between the first and second porous membranes, the first porous membrane comprising a plurality of porous membranes formed therein, the plurality of porous membranes including a first porous membrane side and an opposing second porous membrane side, the first porous membrane side having a first porosity and the second porous membrane side having a second porosity different than the first porosity, the second porous membrane comprising a plurality of porous membranes formed therein, the plurality of porous membranes including a third porous membrane side and an opposing fourth porous membrane side, the third porous membrane side having a third porosity and the fourth porous membrane side having a fourth porosity different than the third porosity, the second porous membrane side and the third porous membrane side facing each other to define the reservoir; and
- a fluid conduit having a first end and a second end, the first end being fluidly coupled to the reservoir and the second end extending outside the body and being insertable into the fluid-filled body cavity such that the fluid from the fluid-filled body cavity is transferrable to the reservoir,
- wherein the first porous membrane is sealed with the second porous membrane such that the first porous membrane side and the fourth porous membrane side are situated relative to each other such that a periphery of the first and second porous membrane sides are exposed to an environment exterior to the device so as to allow drainage of biological fluid at or near the periphery.

21. The device of claim 20, wherein the first porosity is equal to the fourth porosity.

22. The device of claim 20, wherein the second porosity is equal to the third porosity.

* * * * *